United States Patent
Ohsaka et al.

(10) Patent No.: US 11,359,175 B2
(45) Date of Patent: Jun. 14, 2022

(54) SUBSTRATE, STRUCTURE, STRUCTURE-MANUFACTURING METHOD, CELL-SORTING METHOD, CELL-MANUFACTURING METHOD, AND SECRETION-PRODUCING METHOD

(71) Applicants: TOKYO OHKA KOGYO CO., LTD., Kawasaki (JP); CHUGAI SEIYAKU KABUSHIKI KAISHA, Tokyo (JP)

(72) Inventors: Takashi Ohsaka, Kawasaki (JP); Yasuo Suzuki, Kawasaki (JP); Toshiyuki Ogata, Kawasaki (JP); Takuya Noguchi, Kawasaki (JP); Noriyuki Takahashi, Gotemba (JP); Takeshi Baba, Gotemba (JP); Hiroyuki Tsunoda, Gotemba (JP)

(73) Assignees: TOKYO OHKA KOGYO CO., LTD., Kawasaki (JP); CHUGAI SEIYAKU KABUSHIKI KAISHA, Tokyo (JP)

( * ) Notice: Subject to any disclaimer, the term of this patent is extended or adjusted under 35 U.S.C. 154(b) by 317 days.

(21) Appl. No.: 15/764,225

(22) PCT Filed: Sep. 26, 2016

(86) PCT No.: PCT/JP2016/078184
§ 371 (c)(1),
(2) Date: Mar. 28, 2018

(87) PCT Pub. No.: WO2017/057234
PCT Pub. Date: Apr. 6, 2017

(65) Prior Publication Data
US 2018/0282677 A1 Oct. 4, 2018

(30) Foreign Application Priority Data
Sep. 29, 2015 (JP) .............................. JP2015-192311

(51) Int. Cl.
*C12M 1/32* (2006.01)
*G01N 37/00* (2006.01)
(Continued)

(52) U.S. Cl.
CPC .............. *C12M 23/12* (2013.01); *C07K 16/00* (2013.01); *C12M 1/00* (2013.01); *C12M 1/32* (2013.01);
(Continued)

(58) Field of Classification Search
CPC .......... C12M 23/12; C12M 1/34; C12M 1/32; C12M 1/00; C12M 33/00; C12Q 1/02;
(Continued)

(56) References Cited

U.S. PATENT DOCUMENTS 4,894,343 A * 1/1990 Tanaka .................... C12M 23/20
210/498
7,846,389 B2 * 12/2010 Owen ................ G01N 33/5438
422/82.01
(Continued)

FOREIGN PATENT DOCUMENTS

EP 0094193 A2 11/1983
JP B-02-034597 8/1990
(Continued)

OTHER PUBLICATIONS

Harriman WD, et al. "Multiplexed Elispot assay", J Immunol Methods Feb. 28, 2009; 341(1-2):127-134.
(Continued)

*Primary Examiner* — Michael L Hobbs
(74) *Attorney, Agent, or Firm* — Knobbe Martens Olson & Bear LLP

(57) ABSTRACT

In an aspect, the present invention provides a structure, a structure-manufacturing method, a cell-sorting method, or the like. In an aspect, a structure (1) of the present invention
(Continued)

is a structure including a first substrate (10) and a second substrate (20) disposed to face one side of the first substrate (10), in which the first substrate (10) has a plurality of depressions (11) which are open to the other side of the first substrate and each of which has a size that enables each of the depressions to capture one unit of a cell, at least some of the depressions (11) have communication holes (12) which communicate with one side and the other side of the first substrate and each of which has a size that enables secretions secreted from the cell to move through the communication holes, the second substrate (20) can include accumulation portions (13) in which the secretions moving through the communication holes (12) are accumulated, and the accumulation portions (13) can correspond to the depressions (11).

15 Claims, 11 Drawing Sheets

(51) Int. Cl.

| | | |
|---|---|---|
| *C12M 1/34* | (2006.01) | |
| *C12Q 1/02* | (2006.01) | |
| *C12M 1/00* | (2006.01) | |
| *G01N 33/53* | (2006.01) | |
| *G01N 33/50* | (2006.01) | |
| *G01N 33/68* | (2006.01) | |
| *C07K 16/00* | (2006.01) | |
| *C12M 1/26* | (2006.01) | |

(52) U.S. Cl.
CPC ............... *C12M 1/34* (2013.01); *C12M 33/00* (2013.01); *C12Q 1/02* (2013.01); *G01N 33/5008* (2013.01); *G01N 33/5302* (2013.01); *G01N 33/6863* (2013.01); *G01N 37/00* (2013.01); *C07K 2317/10* (2013.01)

(58) Field of Classification Search
CPC ............... G01N 37/00; G01N 33/5302; G01N 33/5008; G01N 33/6863; C07K 2317/5085; C07K 16/00; B01L 2200/0647; B01L 2300/0829; B01L 2300/0861
See application file for complete search history.

(56) References Cited

U.S. PATENT DOCUMENTS

| | | | | |
|---|---|---|---|---|
| 2004/0018615 | A1* | 1/2004 | Garyantes | B01L 3/563 435/305.2 |
| 2004/0023329 | A1* | 2/2004 | Schafer | C12N 15/70 435/69.1 |
| 2005/0106641 | A1 | 5/2005 | Kauvar et al. | |
| 2011/0294678 | A1* | 12/2011 | Jin | G01N 33/54366 506/9 |
| 2015/0111293 | A1 | 4/2015 | Hisashige et al. | |
| 2015/0337355 | A1 | 11/2015 | Araki et al. | |
| 2016/0136552 | A1 | 5/2016 | Nakanishi et al. | |

FOREIGN PATENT DOCUMENTS

| | | |
|---|---|---|
| JP | B-2662215 | 10/1997 |
| JP | A-2006-262825 | 10/2006 |
| JP | B-4148367 | 9/2008 |
| JP | A-2009-034047 | 2/2009 |
| JP | A-2010-281595 | 12/2010 |
| JP | B-5189292 | 4/2013 |
| JP | A-2014-110785 | 6/2014 |
| JP | A-2014-223057 | 12/2014 |
| TW | 201400618 A | 1/2014 |
| WO | WO 02/50260 A2 | 6/2002 |
| WO | WO 2007/035633 A2 | 3/2007 |
| WO | WO 2014/007190 A1 | 1/2014 |
| WO | WO 2014/031997 A1 | 2/2014 |
| WO | WO 2015/012315 A1 | 1/2015 |

OTHER PUBLICATIONS

Harriman WD, et al. "Antibody discovery viamultiplexed single cell characterization" J Immunol Methods. Feb. 28, 2009; 341(1-2):135-145.

International Search Report in Int'l Application No. PCT/JP2016/078184, dated Dec. 27, 2016.

Chen et al., "Microfluidic isolation of highly pure embryonic stem cells using feeder-separated co-culture system", Scientific Reports, vol. 3, No. 1, Aug. 14, 2013 (Aug. 14, 2013), XP055584260.

Huang et al, "An integrated microfluidic platform for in situ cellular cytokine secretion immunophenotyping", Lab on a Chip, vol. 12, No. 20, Jan. 1, 2012 (Jan. 1, 2012), p. 4093, XP055582720.

Huang et al., "An integrated microfluidic platform for in situ cellular cytokine secretion immunophenotyping", 16th International Conference on Miniaturized Systems for Chemistry and Life Sciences, Oct. 28-Nov. 1, 2012, Okinawa, Japan.

Lu et al., "High-Throughput Secretomic Analysis of Single Cells to Assess Functional Cellular Heterogeneity", Analytical Chemistry, vol. 85, No. 4, Feb. 19, 2013 (Feb. 19, 2013), pp. 2548-2556, XP055257119.

Park et al., "Array-Based Analysis of Secreted Glycoproteins for Rapid Selection of a Single Cell Producing a Glycoprotein with Desired Glycosylation", Analytical Chemistry, American Chemical Society, US, vol. 82, No. 13, Jul. 1, 2010 (Jul. 1, 2010), pp. 5830-5837, XP009171374.

Torisawa et al.,"Transwells with Microstamped Membranes Produce Micro patterned Two-Dimensional and Three-Dimensional Co-Cultures", Tissue Engineering. Part C, Methods Dec. 2008, vol. 17, No. 1, Jan. 1, 2011 (Jan. 1, 2011), pp. 61-67, XP055582839.

Torres et al, "Nanowell-Based Immunoassays for Measuring Single-Cell Secretion: Characterization of Transport and Surface Binding", Analytical Chemistry, vol. 86, No. 23, Nov. 17, 2014 (Nov. 17, 2014), pp. 11562-11569, XP055444726.

Search Report issued in European Patent Application No. 16851405.7, dated May 9, 2019.

Office Action in Taiwanese Patent Application No. 105131002 dated Jul. 14, 2020.

Office Action in Japanese Patent Application No. 2019-181550, dated Oct. 6, 2020.

\* cited by examiner

SUBSTRATE, STRUCTURE, STRUCTURE-MANUFACTURING METHOD, CELL-SORTING METHOD, CELL-MANUFACTURING METHOD, AND SECRETION-PRODUCING METHOD

CROSS-REFERENCE TO RELATED APPLICATIONS

This application is the U.S. National Phase under 35 U.S.C. § 371 of International Application PCT/JP2016/078184, filed Sep. 26, 2016, which was published in Japanese as WO 2017/057234 on Apr. 6, 2017, which claims priority to Japanese Patent Application No. 2015-192311, filed Sep. 29, 2015, the entire contents of which are incorporated herein by reference.

TECHNICAL FIELD

In an aspect, the present invention relates to a substrate, a structure, a structure-manufacturing method, a cell-sorting method, a cell-manufacturing method, a secretion-producing method, and the like.

BACKGROUND ART

In recent years, particularly in the field of drug discovery, the target of cell analysis has become subdivided into one cell level from a cell colony level. Attempts are being made to capture cells one by one, identify, sort, collect, and culture the cells, perform gene analysis, and use the sorted cells. As the method for identifying and sorting the cells, a method is adopted in which secretions secreted from the cells are separated, target secretions are detected, and then the cell secreting the target secretions is screened out.

For the single-cell analysis described above, a technique of comprehensively capturing and collectively analyzing cells is required.

As a method for comprehensively capturing cells, PTL 1 describes a substrate and a method in which for the purpose of separating specific cells having different sizes, by using a substrate having opening portions of different sizes within an upper surface and a lower surface, the cells smaller than the opening portions are allowed to pass through the opening portions while the desired cells are retained in the opening portions.

PTL 2 describes, as a substrate for capturing cells and arraying the cells on a plane, a cell-capturing substrate having a plurality of opening portions each of which is for isolating and accommodating one cell and a plurality of through-holes, each of which has a size that prevents cells from passing through the holes, within the bottom surface of the opening portions.

As a technique of the related art that is for collectively analyzing cells by using secretions as an indicator, a FluoroSpot method or a CellSpot method is known.

In the FluoroSpot method, in an aspect, the surface of a microtiter plate is coated with a protein, a porous film is installed in the upper portion of the microtiter plate, and cells are seeded in the microtiter plate and allowed to react with the protein on the surface of the microtiter plate through the porous film. In this technique, the result of binding can be detected using fluorescence-labeled antibodies.

In the CellSpot method, in an aspect, a soluble antigen protein or a membrane protein is caused to bind to polystyrene beads or latex beads, the surface of a microtiter plate is lined with the protein-bound beads, a porous transwell is installed, and cells are then seeded in the microtiter plate and allowed to react with the protein-bound beads on the microtiter plate through the porous film of the transwell. In this technique, the result of binding can be detected using fluorescence-labeled antibodies (see PTL 3 and NPL 1 and 2).

As a method for simultaneously performing single cell analysis for a number of cells, a method is known in which a microchip having wells each of which has a size that allows only one cell to enter each well is used.

PTL 4 describes a microwell array, in which in order to manufacture monoclonal antibodies, cells are cultured in a substrate having wells each of which has a size that allows only one cell to enter each well, and the substances produced from the cells stored in the wells are detected. PTL 4 also describes a cell-screening method using the microwell array.

More specifically, PTL 4 describes a screening method in which at least a portion of the main surface in the vicinity the wells is covered with a covering layer including binding substances that bind to the substances produced from cells, cells are then stored in the wells, and the produced substances and the binding substances in the covering layer are caused to bind to each other and detected.

The microwell array and the cell-screening method using the microwell array described in PTL 4 adopt a constitution in which in the vicinity of the wells storing cells producing substances, there is provided a covering layer of substances binding to the substances. That is, in such a constitution, a culture system of the cells producing substances and a detection system of the substances are integrated on the same plane of a substrate. The produced substances are diffused from the wells to the covering layer in the vicinity of the wells and bind to the binding substances constituting the covering layer. By detecting the binding, the conditions of a number of cells retained on the chip can be simultaneously measured.

CITATION LIST

Patent Literature

[PTL 1] Japanese Examined Patent Application, Second Publication No. H2-34597
[PTL 2] Japanese Patent No. 2662215
[PTL 3] Japanese Patent No. 5189292
[PTL 4] Japanese Patent No. 4148367

Non-Patent Literature

[NPL 1] Harriman W D1, Collarini E J, Cromer R G, Dutta A, Strandh M, Zhang F, Kauvar L M., Multiplexed Elispot assay, J Immunol Methods. 2009 Feb. 28; 341(1-2): 127-34.
[NPL 2] Harriman W D1, Collarini E J, Sperinde G V, Strandh M, Fatholahi M M, Dutta A, Lee Y, Mettler S E, Keyt B A, Ellsworth S L, Kauvar L M., Antibody discovery via multiplexed single cell characterization, J Immunol Methods. 2009 Feb. 28; 341(1-2): 135-45.

SUMMARY OF INVENTION

Technical Problem

The cell-capturing substrates described in PTL 1 and 2 can capture cells. However, unfortunately, secretions secreted from the cells cannot be accumulated, and the cells secreting the target secretions cannot be sorted.

In the FluoroSpot method or the CellSpot method, cells are seeded on a porous film, the produced substances secreted from the cells permeate the film, and by using footprints of the produced substances binding to the solid bottom surface or to beads as indicators, secretory cells present on the upper portion are identified. However, because the cells seeded on the film randomly fall, the cells are not always evenly and singly dispersed, and the formation of a cell cluster constituted with a plurality of cells cannot be avoided. Therefore, it is difficult to secure the singularity of cells.

Furthermore, the cells on the film are not fixed and move from a predetermined position during the operation, which leads to a problem of a risk of cell loss.

In order to fix cells to a predetermined position on the film, a semisolid substance such as methyl cellulose or a certain polymer is used in some cases. However, fixing cells by using a polymer leads to a problem of a risk of reduction in cell viability.

In the porous film of the transwell, pores are randomly formed. It cannot be said that the pores are evenly present in the entire film, and that the pores immediately below the position to which cells have fallen are even. Therefore, unfortunately, no pore may be present in the position where a cell is present, and because the number of pores varies from place to place, it is impossible to secure the evenness of a film permeation amount of the produced substances secreted from cells.

Furthermore, the distance between the bottom surface of the microtiter plate or the bottom surface lined with the protein-bound beads and the transwell is from hundreds of micrometers to several millimeters. Accordingly, secretions are not close to a reaction surface thereof and are diffused. As a result, unfortunately, a clear footprint cannot be formed.

In addition, unfortunately, unless the transwell is removed for analyzing footprints and then accurately installed again in the original position after checking the footprints, it is difficult to identify and collect the secretory cells on the upper portion by using the footprints.

In the CellSpot method, a membrane protein needs to be dissolved and caused to bind to beads. Unfortunately, it is difficult to prepare a soluble membrane protein and to prepare membrane protein-bound beads.

In the method described in PTL 4, in a case where a membrane protein present on the cell surface is used as a binding substance, a membrane protein-expressing cells need to be cultured in the vicinity of wells storing cells. Unfortunately, in a case where the membrane protein-expressing cells are cultured on the wells storing cells, the membrane protein-expressing cells block the wells.

Moreover, unfortunately, the cells producing substances and the membrane protein-expressing cells are likely to be mixed with each other, and contamination is highly likely to occur at the time of collecting the target cells.

The present invention has been accomplished to solve at least some of the aforementioned problems. In an aspect, an object of the present invention is to provide a method which makes it possible to sort cells secreting target secretions in a simple manner with high efficiency, a structure, and a manufacturing method of the structure.

Solution to Problem

In specific aspects that are not limited, the present invention relates to the following inventions, for example.

A first aspect of the present invention is a structure including a first substrate and a second substrate disposed to face one side of the first substrate, in which the first substrate has a plurality of depressions which are open to the other side of the first substrate and each of which has a size that enables each of the depressions to capture one unit of a cell, at least some of the depressions have communication holes which communicate with one side and the other side of the first substrate and each of which has a size that enables secretions secreted from the cell to move through each of the communication holes, the second substrate includes accumulation portions in which the secretions moving through the communication holes are accumulated, and the accumulation portions corresponds to the depressions.

A second aspect of the present invention is a structure including a first substrate and a second substrate which is disposed to face one side of the first substrate and includes a first cell secreting secretions, in which the first substrate has a plurality of depressions which are open to the other side of the first substrate and each of which has a size that enables each of the depressions to capture one unit of a second cell, at least some of the depressions have communication holes which communicate with one side and the other side of the first substrate and each of which has a size that enables secretions secreted from the first cell to move through each of the communication holes, and the second cell is a cell responding to the secretions secreted from the first cell.

A third aspect of the present invention is a structure-manufacturing method including a step 1 of forming a first curable resin film by coating a first support with a first curable resin composition so as to obtain a second substrate, a step 2 of forming a soluble underlayer film on a second support, coating the underlayer film with a second curable resin composition so as to form a second curable resin film, and patterning communication holes on the second curable resin film so as to obtain a supporting layer having patterned communication holes, a step 3 of coating the supporting layer with a third curable resin composition so as to form a third curable resin film and patterning depressions on the third curable resin film so as to obtain a first substrate having patterned depressions, a step 4 of peeling the first substrate from the second support by dissolving the underlayer film, and a step 5 of bonding the first substrate and the second substrate to each other.

A fourth aspect of the present invention is a cell-sorting method for sorting a target cell secreting secretions from a plurality of cells, the method including a step A of dispersing the cells in a first substrate and causing the cells to be captured in depressions, the first substrate including a plurality of depressions each of which has a size that enables each of the depressions to capture one unit of a cell and in which at least some of the depressions have communication holes which communicate with one side and the other side of the first substrate and each of which has a size that enables the secretions secreted from the cells to move through each of the communication holes, a step B of causing the cells to secrete the secretions, moving the secretions through the communication holes, and accumulating the secretions moving through the communication holes in accumulation portions of a second substrate, a step C of performing detection of a change that occurs in the accumulation portions, and a step D of identifying the target cell by using a result of the detection as an indicator.

A fifth aspect of the present invention is a target cell-manufacturing method, including collecting the target cell identified by the cell-sorting method of the present invention.

A sixth aspect of the present invention is a secretion-producing method including a step a of dispersing a group of cells, which are obtained in advance and secrete desired secretions, in a first substrate and causing the cells to be captured in depressions, the first substrate including a plurality of depressions each of which has a size that enables each of the depressions to capture one unit of a cell and in which at least some of the depressions have communication holes which communicate with one side and the other side of the first substrate and each of which has a size that enables the secretions secreted from the cells to move through each of the communication holes, a step b of causing the cells to secrete the secretions, moving the secretions through the communication holes, and accumulating the secretions moving through the communication holes in accumulation portions of a second substrate, a step c of performing detection of a change that occurs in the accumulation portions, a step d of identifying a target cell by using a result of the detection as an indicator, and a step e1 of producing secretions by collecting and culturing the target cell or a step e2 of producing secretions by cloning a polynucleotide encoding the secretions in the target cell and culturing another host cell such that the polynucleotide is expressed.

A seventh aspect of the present invention is use of the curable resin composition in manufacturing the structure of the present invention.

An eighth aspect of the present invention is a substrate including a plurality of depressions which are open to one side and each of which has a size that enables each of the depressions to capture one unit of a cell, in which at least some of the depressions have communication holes which communicate with one side and the other side of a first substrate and each of which has a size that enables secretions secreted from the cell to move through each of the communication holes, the substrate includes accumulation portions in which the secretions moving through the communication holes are accumulated, and the accumulation portions are used by being combined with a second substrate that corresponds to the depressions.

A ninth aspect of the present invention is a structure including the substrate of the present invention.

Advantageous Effects of Invention

In an aspect, according to the present invention, a method which makes it possible to sort a cell secreting target secretions in a simple manner with high efficiency, a structure, a manufacturing method of the structure, and the like can be provided.

DESCRIPTION OF EMBODIMENTS

Figure 1:
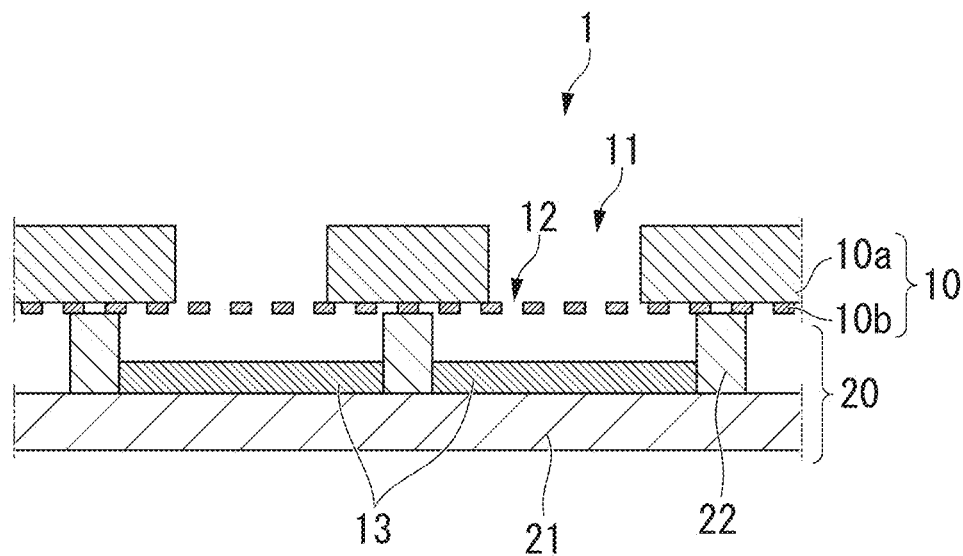
FIG. 1 is a schematic view showing an embodiment of a structure of the present invention.

Hereinafter, preferred aspects of the present invention that are not limited will be described.

Structure

First Embodiment

A structure 1 of the present embodiment is a structure including a first substrate 10 and a second substrate 20 which is disposed to face one side of the first substrate 10. The first substrate 10 has a plurality of depressions 11 which are open to the other side of the first substrate 10 and each of which has a size that enables each of the depressions to capture one unit of a cell. At least some of the depressions 11 have communication holes 12 which communicate with one side and the other side of the first substrate 10 and each of which has a size that enables secretions secreted from the cell to move through each of the communication holes. The second substrate 20 can include accumulation portions 13 in which the secretions moving through the communication holes 12 are accumulated. The accumulation portions 13 can correspond to the depressions 11.

The structure 1 is preferably a structure used for dispersing cells, causing the cells to be captured in the depressions 11, accumulating the secretions secreted from the cells in the accumulation portions 13 through the communication holes 12, and detecting a change that occurs in the accumulation portions 13.

<First Substrate Including Depressions for Storing Cells>

As shown in FIG. 1, the first substrate 10 includes a layer 10*a* in which the depressions 11 are patterned, and a layer 10*b* in which the communication holes 12 are patterned.

Figure 2:
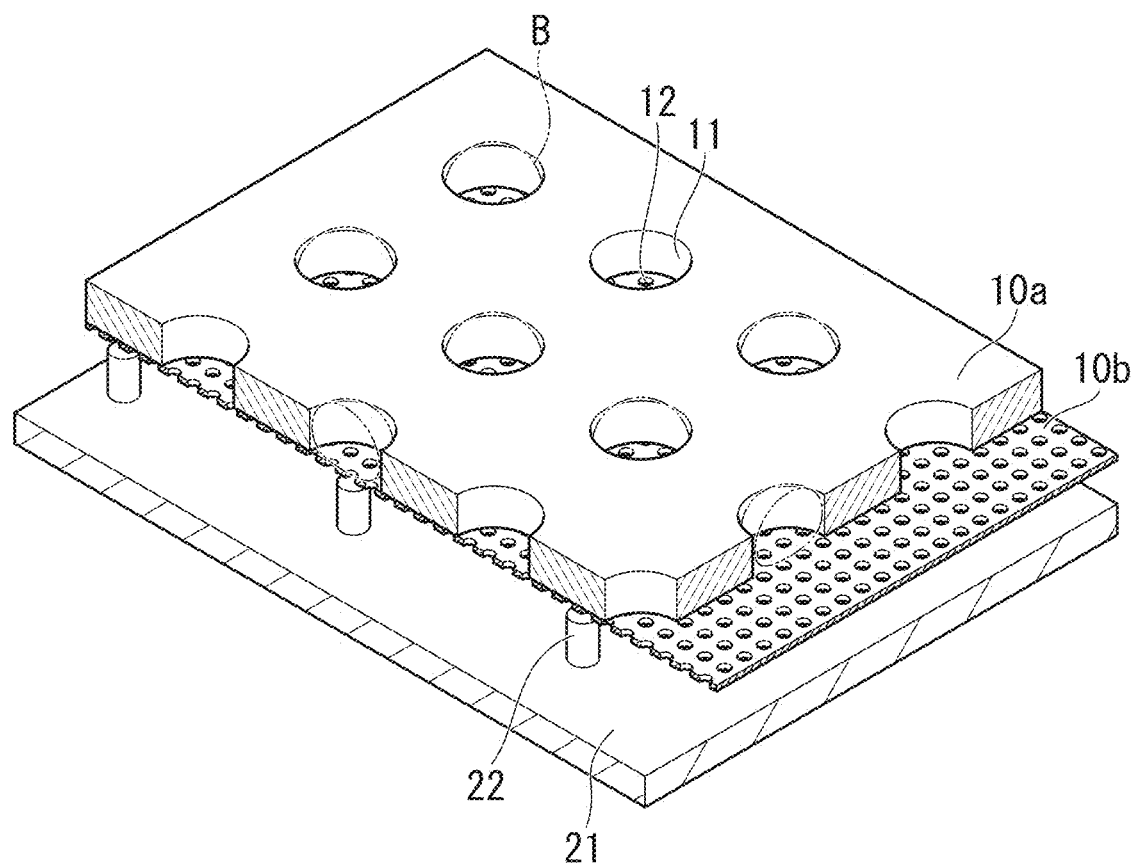
FIG. 2 is a perspective view showing an embodiment of the structure of the present invention.

As shown in FIG. 2, in the structure 1, for example, a plurality of depressions 11 may be disposed lengthwise and breadthwise at equal intervals.

The thickness of the first substrate is preferably 5 to 100 µm, and more preferably 10 to 50 µm.

In FIG. 2, B represents one unit of a cell. As shown in FIG. 2, the shape of the depressions 11 is not particularly limited as long as the shape enables each of the depressions to capture one unit of a cell. The shape of the depressions 11 may be a cylindrical shape or may be a polyhedron constituted with a plurality of faces (for example, a cuboid, a hexagonal prism, an octagonal prism, or the like), an inverted cone, an inverted pyramid (an inverted triangular pyramid, an inverted quadrangular pyramid, an inverted pentagonal pyramid, an inverted hexagonal pyramid, or an inverted polyhedral pyramid having seven or more faces), and the like other than the cylindrical shape. Furthermore, the shape of the depressions 11 may be a shape obtained by combining two or more shapes among the above shapes.

For example, some of the depressions 11 may have a cylindrical shape, and the rest of them may have an inverted cone shape. In a case where the depressions 11 have an inverted cone shape or an inverted pyramid shape, the bottom surface thereof becomes the opening of the depressions 11. In this case, the depressions 11 may have a shape obtained by cutting off a portion of the apex of the inverted cone or the inverted pyramid (in this case, the bottom of the depressions becomes flat). In a case where the depressions 11 have a cylindrical shape or a cuboidal shape, the bottom of the depressions 11 is generally flat. However, in this case, the bottom of the depressions 11 may be a curved surface (convex surface or concave surface). In a case where the depressions 11 have a shape obtained by cutting off a portion of the apex of an inverted cone or an inverted pyramid, the bottom of the depressions can also be a curved surface.

In the present embodiment, one unit of a cell may mean one cell or a single cluster of cells having the same trait. The single cluster of cells can include at least two or more cells. That is, for example, one unit of a cell may be one colony derived from the same cell.

The dimensions of the depressions 11 can be appropriately determined in consideration of a suitable ratio between the diameter of a cell to be stored in the depressions 11 and the dimensions of the depressions 11. It is preferable that the depressions 11 are patterned such that the form, density, and the like thereof are controlled.

Furthermore, the shape and dimensions of the depressions 11 can be appropriately determined in consideration of the type of the cell (shape, dimensions, and the like of the cell) that should be stored in the depressions 11, such that one unit of a cell is stored in one depression.

For example, in order to cause one cell to be stored in one depression, the diameter of the largest circle inscribed in the planar shape of each of the depressions 11 is preferably within a range of 50% to 200%, more preferably within a range of 80% to 190%, and even more preferably within a range of 80% to 180% of the diameter of a cell to be stored in one depression 11.

The depth of each of the depressions 11 is preferably within a range of 50% to 400%, more preferably within a range of 80% to 190%, and even more preferably within a range of 80% to 180% of the diameter of a cell to be stored in one depression 11.

The number of depressions 11 included in the first substrate 10 is not particularly limited. For example, the number of depressions 11 per 1 $cm^2$ is preferably within a range of 2,000 to 1,000,000.

The aperture ratio of the depressions 11 included in the first substrate 10 is not particularly limited, and is preferably within a range of 1% to 90% for example.

In a case where the depressions 11 have a cylindrical shape, regarding the dimensions, the diameter thereof is preferably 1 to 100 μm, more preferably 2 to 50 μm, even more preferably 3 to 25 μm, and particularly preferably 4 to 20 μm.

Furthermore, in a case where the depressions 11 have a cylindrical shape, the depth thereof is preferably 1 to 100 μm, more preferably 2 to 70 μm, even more preferably 3 to 50 μm, and particularly preferably 4 to 30 μm. From the viewpoint of practical use, it is preferable that the depth is equal to or greater than 1 μm because then one cell is easily captured. In contrast, it is not preferable that the depth is equal to or smaller than 100 μm, because then a plurality of cells may be captured.

The cell constituting one unit of a cell captured by each of the depressions 11 of the first substrate 10 is not particularly limited as long as the cell secretes secretions. Examples of the cell include animal cells (for example, cells derived from a human being, a mouse, a camel, a monkey, a bird, or a shark); plant cells; insect cells; fungus such as yeast; bacteria such as *E. coli*; and the like.

Examples of the cell also include proteins obtained by inserting a secretory protein, a secretory polypeptide, or a secretion signal into the aforementioned cells, expression strains obtained by introducing a gene encoding a polypeptide into the aforementioned cells, and the like.

The secretions may be naturally occurring secretions or non-naturally occurring secretions obtained using genetic engineering.

The secretions are not limited and preferably a single type of secretions. Examples thereof include cytokines such as immunoglobulin (for example, immunoglobulin G (IgG) or immunoglobulin M (IgM), interleukin (IL-2, IL-7, IL-12, IL-15, or the like), chemokine, interferon (IFN-γ or the like), a hemopoietic factor (a colony stimulating factor, a granulocyte colony stimulating factor, erythropoietin, or the like), a cell growth factor (an epithelial growth factor, a fibroblast growth factor, a platelet-derived growth factor, a hepatocyte growth factor, a transforming growth factor, or the like), a cytotoxic factor (a tumor necrosis factor or lymphotoxin), adipokines (leptin, a tumor necrosis factor, and the like secreted from adipose tissue), and a neurotrophic factor (nerve growth factor or the like), metabolites of microorganisms such as an antibiotic or a pigment, a peptide hormone or a steroid hormone secreted from the aforementioned secretory cells, hormones of microorganisms, secretory proteins, proteins into which a secretion signal is inserted, and the like. Alternatively, the secretions may be obtained by modifying the aforementioned secretions through genetic engineering. In an embodiment, the secretions are preferably antibody molecules.

Examples of naturally occurring antibody molecules may include immunoglobulin G (IgG) or immunoglobulin M (IgM).

Examples of non-naturally occurring antibody molecules may include antibody fragments such as Fab, scFv, and Diabody, single domain antibodies (Methods in Molecular Biology Volume, 911, 2012), artificial protein molecules having properties similar to those of antibodies (Skrlec K, Strukelj B, Berlec A. Non-immunoglobulin scaffolds: a focus on the it targets, Trends Biotechnol., 2015, Apr. 27), and the like.

Examples of cells usable in the present embodiment include cells secreting antibody molecules, cytokine-producing cells, and hormone-secreting cells.

The cells secreting antibody molecules are not limited. In a case where the antibody molecules are naturally occurring molecules, examples of the cells include animal cells such as an antibody-producing cell like B cell, a hybridoma fused with a myeloma cell, and an expression cell into which a polynucleotide encoding antibody molecules is introduced, and the like. In a case where the antibody molecules are non-naturally occurring molecules, examples of the cells include fungi such as yeast, bacteria such as *E. coli*, and the like other than animal cells.

The cytokine-producing cells are not limited, and examples thereof include a macrophage, B cell, T cell, NK cell, NKT cell, a dendrite cell, a hepatic Kupffer cell, a stroma cell, a fibroblast, an endothelial cell, and the like.

The hormone-secreting cells are not limited, and examples thereof may include an anterior pituitary cell, a somatotropin-producing cell, a lactotropin-producing cell, a thyroid stimulating hormone-producing cell, a gonadotropic hormone-producing cell, a corticotropin-producing cell, an intermediate pituitary cell, a cell secreting a melanocyte-stimulating hormone, an oxytocin-secreting cell, a vasopressin-secreting cell, a serotonin-secreting cell, an endorphin-secreting cell, a somatostatin-secreting cell, a gastrin-secreting cell, a secretin-secreting cell, a cholecystokinin-secreting cell, an insulin-secreting cell, a glucagon-secreting cell, a bombesin-secreting cell, a thyroid cell, a thyroid epithelial cell, a parafollicular cell, a parathyroid cell, a parathyroid principal cell, an oxyphilic cell, an adrenal gland cell, a chromaffin cell, a steroid hormone (mineralocorticoid or glucocorticoid)-producing cell, a testosterone-secreting cell, an estrogen-secreting cell, a progesterone-secreting cell, a juxtaglomerular apparatus cell of the kidneys, a macula densa cell of the kidneys, a peripolar cell of the kidneys, a mesangial cell of the kidneys, and the like.

<Communication Hole>

The dimensions of the communication holes 12 can be appropriately determined in consideration of a suitable ratio between the diameter of one unit of a cell to be stored in each of the depressions 11, the dimensions of the depressions 11, and the dimensions of the secretions which should be moved through the communication holes 12. It is preferable that the communication holes 12 are patterned such that the shape, size, density, and the like of the pores are controlled. It is preferable that the communication holes are controlled, because then the evenness of a permeation amount of the secretions secreted from cells can be easily secured.

Specifically, the number, the position, shape, and size of the communication holes 12, and the like are not particularly limited, as long as each of the communication holes 12 has a size that enables one unit of a cell to be stored without passing through the holes and enables the secretions from the cell to move through the holes. It is preferable that the communication holes 12 are patterned such that the shape, size, density, and the like of the pores are controlled.

Figure 4:
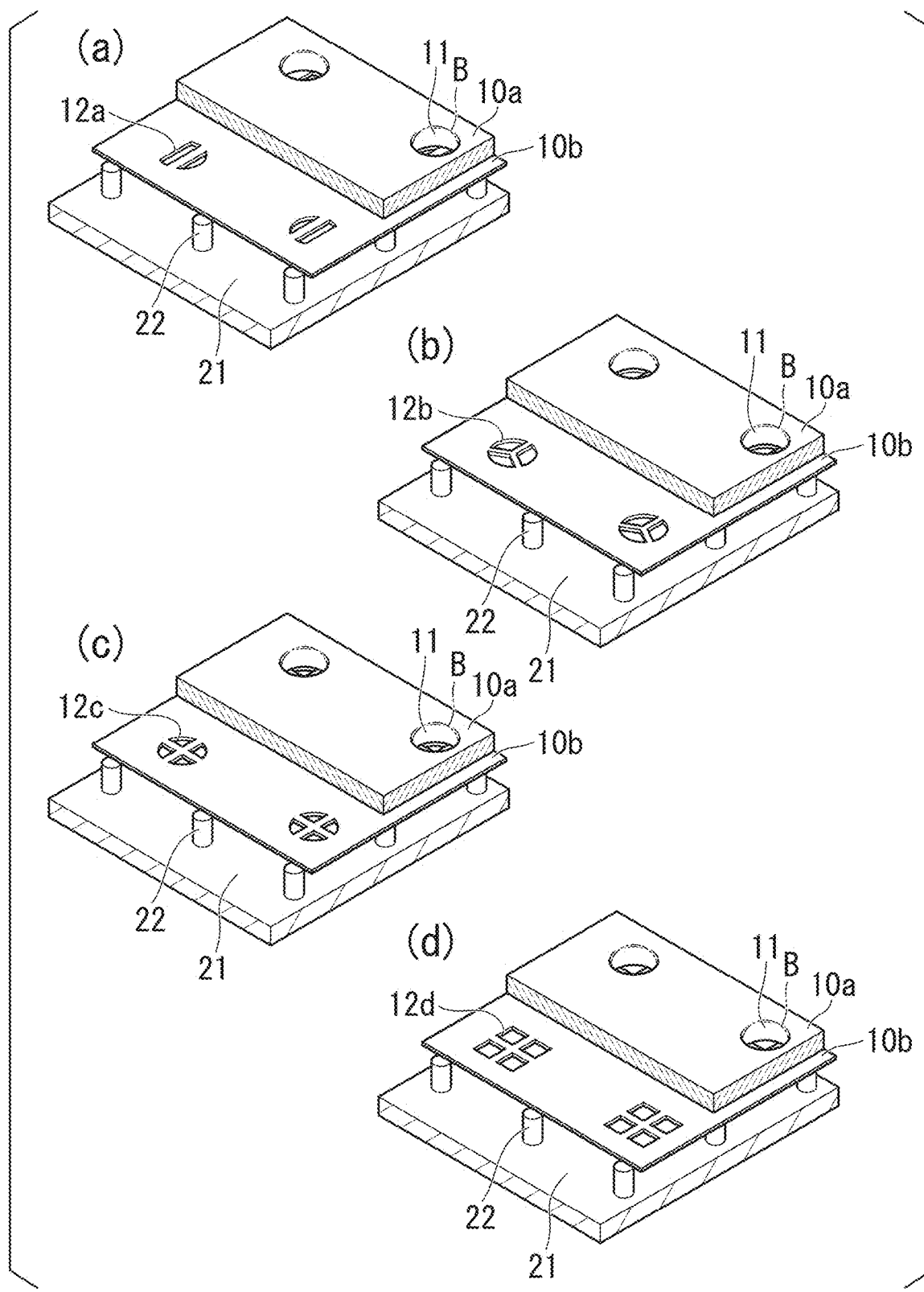
FIG. 4 is a schematic view showing an embodiment of the structure of the present invention.

For example, as shown in FIG. 2, in a case where the depressions 11 have a cylindrical shape, the bottom of the depressions 11 may be provided with a plurality of cylindrical communication holes 12 having a diameter smaller than the diameter of the depressions 11. Furthermore, as shown in FIG. 4, in a case where the depressions 11 have a cylindrical shape, the bottom of the depressions 11 may be provided with communication holes having shapes represented by 12a to 12d in FIGS. 4(a) to 4(d). For example, in a case where the communication holes 12 have a circular shape, the diameter thereof is preferably 10 to 2,000 nm, more preferably 100 to 1,500 nm, and even more preferably 200 to 1,000 nm. In a case where the communication holes 12 have a palisade shape, the width thereof is preferably 10 to 2,000 nm, more preferably 10 to 1,500 nm, and even more preferably 10 to 1,000 nm. In a case where the communication holes 12 have a lattice shape, the length of one side thereof is preferably 10 to 2,000 nm, more preferably 10 to 1,500 nm, and even more preferably 10 to 1,000 nm. The aspect ratio of the communication holes is preferably 1 to 10, and more preferably 1 to 5.

<Second Substrate that can Include Accumulation Portions in which Secretions Secreted from Cell are Accumulated>

As shown in FIG. 1, the structure 1 of the present embodiment has the second substrate 20 that can include accumulation portions 13 in which the secretions secreted from one unit of a cell captured in the first substrate 10 are accumulated.

In the present embodiment, "secretions are accumulated" may mean that the secretions come into contact with, stay in, bind to, are gathered in, and/or are accumulated in the accumulation portions. By the contact between the secretions and the accumulation portions and the like, a certain change in the accumulation portion 13 can be detected. In the present specification, in a case where a certain change occurs in the accumulation portions 13 due to the contact between secretions and the accumulation portions 13 and the like, such a case may be described as "the accumulation portions 13 respond to secretions". For example, in a case where the accumulation portions 13 include cells, examples of aspects in which the accumulation portions respond to secretions include aspects in which the contact between the accumulation portions 13 and secretions result in, for example, the change of the form of the cells included in the accumulation portions 13, the death of cells, the change of cell growth ability, the change of the amount of substance (ion, pH, or the like) in the cells, the activation of gene transcription in the cells, and the like.

As secretory cells added to the first substrate 10, for example, it is possible to use feeder cells (for example, fibroblasts derived from a mouse fetus, JK1 cells, SNL76/7 cells, or cells obtained by modifying these cells by genetic engineering). In this case, as cells to be incorporated into the accumulation portions 13, for example, cells having a differentiation capacity (for example, iPS cells, ES cells, mesenchymal stem cells, stem cells derived from a biological body, or cells obtained by modifying these cells by genetic engineering) may be used.

The second substrate 20 includes a substrate body 21, pillars 22 supporting the first substrate 10, and the accumulation portions 13. In a case where the structure 1 has means for supporting the first substrate 10, the pillars may not be present. Alternatively, those skilled in the related art can understand that in a case where the structure 1 has pillars, as long as the pillars can support the first substrate 10 and the objects of the present invention can be achieved, the number, the position, shape, size of the pillars, and the like are not particularly limited.

In order to rapidly evaluate the secretions, which are secreted from one unit of a cell stored in each of the depressions 11 of the first substrate 10, in the second substrate 20 by using the structure 1 of the present embodiment, it is preferable the evaluation position of the secretions in the second substrate 20 corresponds to the position of the cell secreting the secretions (more preferably, one-to-one correspondence).

That is, in the structure 1 of the present embodiment, it is preferable that by the means for supporting the first substrate 10 such as pillars, the positions of the first substrate 10 and the second substrate 20 are fixed.

It is preferable that the accumulation portions 13 include a substance having an affinity with the secretions secreted from one unit of a cell captured by the first substrate 10.

"Having affinity" may mean that the substance directly binds to the secretions or indirectly binds to the secretions through another molecule.

The "substance" included in the accumulation portions 13 may mean various substances binding to secretions secreted from cells, and may include cells, biological polymers such as a polynucleotide, an antibody, a peptide, and a protein, or various chemical substances. Examples of the cells are the same as those exemplified above in <First substrate including depressions for storing cells>.

For example, in a case where the secretions are antibodies, the "substance" included in the accumulation portions 13 include various substances corresponding to antigens, and examples thereof preferably include a peptide or a protein. In this case, examples of the accumulation portions 13 include an antigen peptide-fixed layer or an antigen protein-fixed layer.

Furthermore, the accumulation portions 13 may be a cell layer lined with cells that exogenously or endogenously express antigens. In a case where the antigens are expressed in the nuclei or in the cytoplasm, it is preferable to lyse or grind the cell membrane and use the resultant showing the antigens. In addition, cells that exogenously or endogenously express antigens on the cell membrane may be used. These cells are excellent because the antibodies can have access to the antigens even though the cell membrane is not lysed or ground.

The structure 1 of the present embodiment is suitably used for sorting cells producing antibodies against membrane proteins.

In the present embodiment, "membrane protein" means a protein attached to a biological membrane. The membrane protein includes an intrinsic membrane protein which penetrates a lipid bilayer membrane or binds to a lipid bilayer through a fatty acid chain or the like, and a peripheral membrane protein which binds to a hydrophilic portion of a lipid bilayer or to other membrane proteins through a covalent bond. In the present embodiment, the membrane protein may be a multi-pass protein or a single-pass protein.

Examples of the membrane protein include a G protein-coupled receptor (GPCR), a ligand-gated ion channel, a voltage-gated ion channel, a transporter, and the like.

Figure 3:
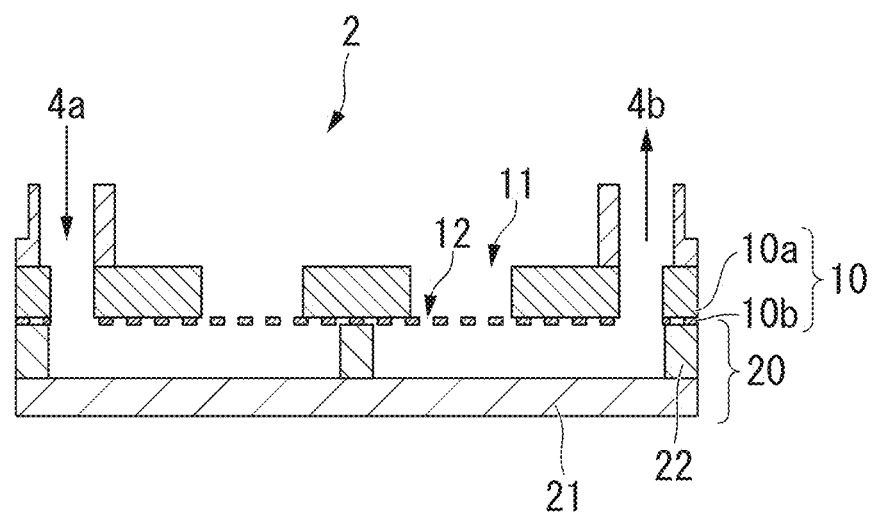
FIG. 3 is a schematic view showing an embodiment of the structure of the present invention.

It is preferable that the second substrate 20 has a flow channel structure for removing the substance nonspecifically binding to the accumulation portions 13. For example, as shown in FIG. 3, the structure (structure 2) may have connection ports 4a and 4b.

The flow channel structure may be used for allowing a substance for detection which is for detecting a change occurring in the aforementioned accumulation portions to flow, for example, for allowing a substance for detection which is for detecting the secretions binding to the accumulation portions 13 to flow.

For example, at the time of detecting secretions, a washing solution is allowed to flow from the connection port 4a, and the substance nonspecifically binding to the accumulation portions 13 is discharged from the connection port 4b. Then, by allowing the substance for detection, which is for detecting secretions, to flow from the connection port 4a, the substance for detection is caused to bind to secretions. Thereafter, a washing solution is allowed to flow from the connection port 4a, and the substance for detection having not bound to secretions is discharged from the connection port 4b.

In a case where the second substrate 20 has the flow channel structure described above, it is possible to conveniently detect the secretions binding to the accumulation portions 13.

The substance for detection which is for detecting secretions may flow from the first substrate to the second substrate together with a medium or the like through the communication holes 12.

As the substance for detection, a labeled substance is preferable which has a secretion recognition site different from a secretion recognition site included in the accumulation portions. For example, in a case where the secretions are antibodies, examples of the substance for detection may include labeled secondary antibodies specific to the Fc portion of antibodies and the like.

Examples of labeling include enzymatic labeling, fluorescence labeling, and labeling using biotin or a radioactive material.

In a case where cells are used as the accumulation portions 13, the flow channel structure of the second substrate 20 can be flow channels of a culture solution for culturing cells.

In a case where the structure is used for sorting antibody-producing cells recognizing a membrane protein as an antigen, each of the accumulation portions is preferably a layer including membrane protein-expressing cells, and more preferably a layer formed of membrane protein-expressing cells.

In order to obtain monoclonal antibodies against the membrane protein, the membrane protein needs to immunize an experimental animal while maintaining the original three-dimensional structure of the membrane protein. In a case where a surfactant is used at the time of extracting membrane proteins from a cell membrane, the three-dimensional structure of the membrane proteins is destroyed. On the other hand, in a case where a surfactant is not used, unfortunately, the hydrophobic regions in the membrane proteins are aggregated with each other. Accordingly, generally, it is impossible to easily prepare membrane proteins maintaining a three-dimensional structure as antigens.

In contrast, in a case where membrane proteins expressed on the surface of a cell membrane are used as antigens, it is possible to form a complex with secreted antibodies in a state of maintaining the three-dimensional structure and to evaluate the titer of the secreted antibodies.

As the membrane protein-expressing cells, cells that originally highly express a target membrane protein may be used, or a cell strain artificially forced to express a target membrane protein may be used. Examples of the cell strain artificially forced to express a target membrane protein include a transient expression cell strain and a stable expression cell strain. It is preferable to use the stable expression cell strain because it is easy to handle this strain.

In the present embodiment, the first substrate and the second substrate are filled with the same liquid (typically, for example, the liquid may be a medium, a buffer such as PBS or physiological saline, or the like). Through the communication holes, the liquid flows to the second substrate from the first substrate or to the first substrate from the second substrate. While the liquid is flowing, the substances (for example, secretions) in the medium travels between the first substrate and the second substrate.

Figure 5:
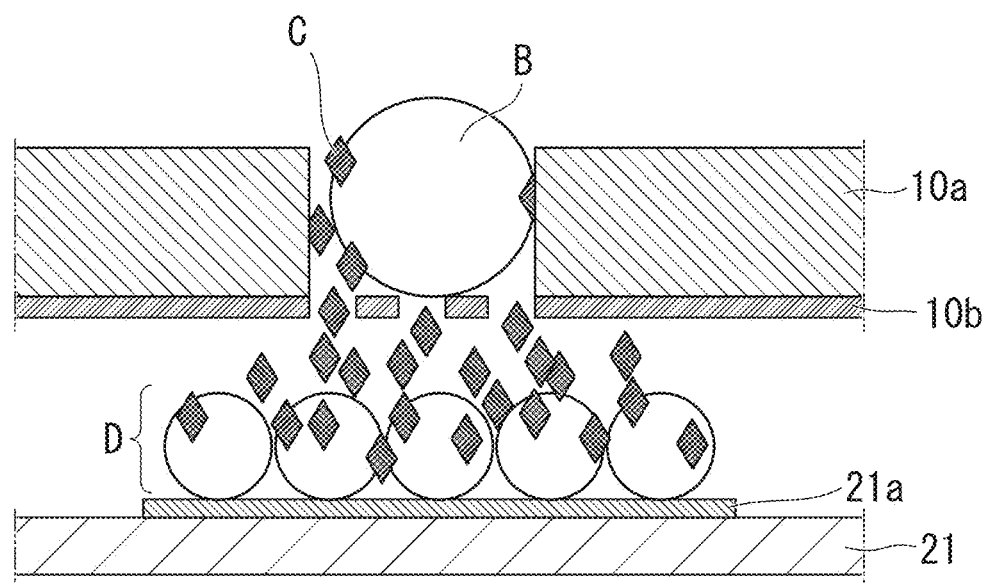
FIG. 5 is a schematic view showing an embodiment of the structure of the present invention.

For example, as shown in FIG. 5, in the structure of the present embodiment, the first substrate captures a cell B, and a secretion C from the cell B passes through the communication holes and moves to the second substrate. Therefore, the secretion C from the cell B can be separated from the cell B. Accordingly, the cell B captured by the first substrate 10 and a membrane protein-expressing cell D to which the secretion C from the cell B will bind can be separately cultured.

As a result, according to the structure of the present embodiment, in a case where a membrane protein-expressing cell in which a membrane protein is exposed on the cell surface is used as a substance having affinity with the secretions, the cell B and the membrane protein-expressing cell D are less likely to be mixed with each other, and contamination may hardly occur at the time of culture. Consequently, the structure of the present embodiment is particularly useful for screening an antibody-producing cell by using a membrane protein-expressing cell.

Furthermore, the membrane protein-expressing cell and the cell secreting secretions are cultured in different layers. That is, a culture system and a detection system that have been integrated in the related art are separated from each other. Accordingly, a phenomenon, in which the membrane protein-expressing cell blocks wells, having been an issue of screening performed using a microwell array in the related art does not occur.

According to the structure of the present embodiment, in a case where the structure has an array of depressions each of which can store one unit of a cell, the seeded cells are stored in the depressions and evenly and singly arranged. Therefore, a problem in that the cells seeded on the film cannot be evenly and singly dispersed, which is a problem of a transwell film of the related art, does not occur.

According to the structure of the present embodiment, in a case where one unit of a cell is fixed to a predetermined position by being stored in a depression, a substance for fixing one unit of a cell is not required. Therefore, a problem of a reduction of cell viability, which has been a problem caused by the method of using a substance such as a polymer or methyl cellulose for fixing, does not occur.

According to the structure of the present embodiment, in a case where the communication holes of the depressions each storing one unit of a cell are patterned and hence the shape, size, density, and the like of the pores are controlled, the evenness of the permeation amount of the secretions secreted from one unit of a cell is secured. Therefore, the problems of the transwell film of the related art, which includes problems in that pores immediately below the position to which cells have fallen are not always even, no pore may be present in the position in which a cell is present, the number of cells varies, and the evenness of the film permeation amount of produced substances secreted from cells cannot be secured, do not occur.

Furthermore, according to the structure of the present embodiment, in a case where the interval between the first substrate and the second substrate is fixed within a range of several micrometers to tens of micrometers, the secretions to be diffused are accumulated in a narrow region at a high concentration. Therefore, at the time of detecting the secretions by using a labeling substance, the signal becomes clear, and the detection sensitivity is improved.

In addition, according to the structure of the present embodiment, in a case where the positions of the first substrate and the second substrate are fixed, the problems of the FluoroSpot method or the CellSpot method using a transwell, which includes a problem in that cells move and are lost during the operation and a phenomenon in which the position of a secretory cell becomes different from the position of a footprint made by a substance produced from the secretory cell, do not occur.

In structures of the related art, cells have been stored in depressions by free fall exploiting the weight of the cells or by forced fall exploiting centrifugal force, and these methods have a problem of a low storage rate. According to the structure of the present embodiment, a flow of a liquid from the depressions to the communication holes can be created. Therefore, due to the flow of the liquid, cells are easily stored in the depressions, and the storage rate is improved.

In a case where an attempt is made to collect cells in structures of the related art, by the aspiration of the cells from depressions, it is difficult to create a flow of a liquid containing the cells, and a problem occurs in which a target cell is collected at a low success rate. In contrast, according to the structure of the present embodiment, through the communication holes of the depressions, a flow of a liquid from the second substrate can be created. Therefore, the success rate of collecting cells is further improved compared to the structures of the related art.

The material of the structure of the present embodiment is not particularly limited. From the viewpoint of making it easy to observe cells, transparent materials are preferable. Particularly, it is preferable that the substrate body 21 and a layer 21a are made of a transparent material.

Alternatively, for example, in a case where a certain change occurring in the accumulation portions 13 is observed using a fluorescent label as an indicator, materials hardly having autofluorescence are preferable. Specifically, it is possible to use glass and general transparent resins hardly having autofluorescence such as PET, PMMA, PC, a cycloolefin polymer (COP), and epoxy. From the viewpoint of cell culture, it is preferable that the material of the structure of the present embodiment is non-cytotoxic and has undergone a hydrophilizing treatment.

From the viewpoint of forming depressions each of which has a size that enables each of the depressions to capture one unit of a cell and forming communication holes each of which has a size that enables secretions from a cell to move through each of the communication holes, it is preferable that the structure of the present embodiment is obtained by polymerizing a curable resin composition (hereinafter, referred to as "photosensitive resin composition" in some cases) that is easily microfabricated.

The curable resin composition has a property of being cured by causing cross-linking by being irradiated with active energy rays such as ultraviolet rays. As the curable resin composition, those used for a negative photoresist, a negative dry film resist, micro resin molding having a microstructure, and the like are preferably used. Herein, a resin pattern is a cured product obtained by curing the curable resin composition in a desired shape by a photolithography method.

In a case where the curable resin composition is used for micro resin molding and the like, first, the surface of a substrate in which a resin pattern will be formed is coated with the curable resin composition, and solvent components contained in the curable resin composition are volatilized, thereby preparing a resin film. Then, a photomask that will become the shape of the pattern to be formed is placed on the surface of the resin film and irradiated with active energy rays such as ultraviolet rays. Thereafter, through a development step and a post-baking step which is performed if necessary, a resin pattern is formed on the surface of the substrate. The resin pattern can be used in the structure of the present embodiment.

As the aforementioned curable resin composition, for example, it is possible to adopt resin compositions generally used for micro resin molding, such as a photocurable composition which contains a functional epoxy-novolac resin, a cationic photopolymerization initiator such as a triaryl sulfonium salt, and a diluent being able to react with an epoxy functional group and becomes a hardly peeled resin after being completely cured; and a photocurable composition which contains a polyfunctional bisphenol A formaldehyde novolac resin, triphenylsulfonium hexafluoroantimonate as an acid generator, and PGMEA as a solvent and becomes a resin being able to form a thick film.

Furthermore, in a case where the photosensitive (curable) resin composition is prepared by combining an epoxy resin with a specific acid generator, and a resin pattern is formed using the curable resin composition, it is possible to form a resin pattern, which undergoes a small extent of volumetric shrinkage at the time of heating and curing and has a shape with a high aspect ratio, with high sensitivity.

Examples of the curable (photosensitive) resin composition include a photosensitive resin composition containing (a) polyfunctional epoxy resin and (b) cationic polymerization initiator.

[(a) Polyfunctional Epoxy Resin]

The polyfunctional epoxy resin used in the present embodiment is a resin having two or more epoxy groups in one molecule. As the polyfunctional epoxy resin, any epoxy resin may be used as long as it is an epoxy resin in which the number of epoxy groups contained in one molecule is enough for curing a resin film formed of the curable resin composition. As the polyfunctional epoxy resin, a phenol novolac-type epoxy resin, an o-cresol novolac-type epoxy resin, a triphenyl novolac-type epoxy resin, and a bisphenol A novolac-type epoxy resin are preferable.

The functionality represented by the number of epoxy groups contained one molecule of the polyfunctional epoxy resin is preferably equal to or greater than 2, and more preferably 3 to 12. It is preferable that the polyfunctionality of the polyfunctional epoxy resin is equal to or greater than 3, because then a resin pattern having a high aspect ratio and high resolution can be formed. It is preferable that the polyfunctionality of the polyfunctional epoxy resin is equal to or smaller than 12, because then the resin synthesis is easily controlled, and the internal stress of the resin pattern can be inhibited from excessively increasing.

The mass average molecular weight of the polyfunctional epoxy resin is preferably 300 to 5,000, and more preferably 500 to 4,000. It is preferable that the mass average molecular weight of the polyfunctional epoxy resin is equal to or greater than 300, because then it is possible to inhibit the curable resin composition from causing a thermal flow before being cured by being irradiated with active energy rays. It is preferable that the mass average molecular weight of the polyfunctional epoxy resin is equal to or smaller than 5,000, because then an appropriate dissolution rate can be obtained at the time of patterning and development.

The content of the polyfunctional epoxy resin in the photosensitive resin composition with respect to the total solid content of the composition is preferably 10% by mass to 99.9% by mass, and more preferably 30% by mass to 99.9% by mass. In a case where the content of the polyfunctional epoxy resin is within the above range, by coating a substrate with the composition, a photosensitive resin film having appropriate hardness is obtained with high sensitivity.

[(B) Cationic Polymerization Initiator]

Next, the cationic polymerization initiator will be described. The cationic polymerization initiator used in the present embodiment is a compound which generates a cation by being irradiated with active energy rays such as ultraviolet rays, far-ultraviolet rays, excimer laser rays of KrF or ArF, X-rays, and electron beams. The cation can become a polymerization initiator.

Examples of the cationic initiator include 4-(2-chloro-4-benzoylphenylthio)phenyl diphenylsulfonium hexafluoroantimonate, 4-(2-chloro-4-benzoylphenylthio)phenyl bis(4-fluorophenyl)sulfonium hexafluoroantimonate, 4-(2-chloro-4-benzoylphenylthio)phenyl bis(4-chlorophenyl)sulfonium hexafluoroantimonate, 4-(2-chloro-4-benzoylphenylthio)phenyl bis(4-methylphenyl)sulfonium hexafluoroantimonate, 4-(2-chloro-4-benzoylphenylthio)phenyl bis(4-(β-hydroxyethoxy)phenyl)sulfonium hexafluoroantimonate, 4-(2-methyl-4-benzoylphenylthio)phenyl bis(4-fluorophenyl)sulfonium hexafluoroantimonate, 4-(3-methyl-4-benzoylphenylthio)phenyl bis(4-fluorophenyl)sulfonium hexafluoroantimonate, 4-(2-fluoro-4-benzoylphenylthio)phenyl bis(4-fluorophenyl)sulfonium hexafluoroantimonate, 4-(2-methyl-4-benzoylphenylthio)phenyl bis(4-fluorophenyl)sulfonium hexafluoroantimonate, 4-(2,3,5,6-tetramethyl-4-benzoylphenylthio)phenyl bis(4-fluorophenyl)sulfonium hexafluoroantimonate, 4-(2,6-dichloro-4-benzoylphenylthio)phenyl bis(4-fluorophenyl)sulfonium hexafluoroantimonate, 4-(2,6-dimethyl-4-benzoylphenylthio)phenyl bis(4-fluorophenyl)sulfonium hexafluoroantimonate, 4-(2,3-dimethyl-4-benzoylphenylthio)phenyl bis(4-fluorophenyl)sulfonium hexafluoroantimonate, 4-(2-methyl-4-benzoylphenylthio)phenyl bis(4-chlorophenyl)sulfonium hexafluoroantimonate, 4-(3-methyl-4-benzoylphenylthio)phenyl bis(4-chlorophenyl)sulfonium hexafluoroantimonate, 4-(2-fluoro-4-benzoylphenylthio)phenyl bis(4-chlorophenyl)sulfonium hexafluoroantimonate, 4-(2-methyl-4-benzoylphenylthio)phenyl bis(4-chlorophenyl)sulfonium hexafluoroantimonate, 4-(2,3,5,6-tetramethyl-4-benzoylphenylthio)phenyl bis(4-chlorophenyl)sulfonium hexafluoroantimonate, 4-(2,6-dichloro-4-benzoylphenylthio)phenyl bis(4-chlorophenyl)sulfonium hexafluoroantimonate, 4-(2,6-dimethyl-4-benzoylphenylthio)phenyl bis(4-chlorophenyl)sulfonium hexafluoroantimonate, 4-(2,3-dimethyl-4-benzoylphenylthio)phenyl bis(4-chlorophenyl)sulfonium hexafluoroantimonate, 4-(2-chloro-4-acetylphenylthio)phenyl diphenylsulfonium hexafluoroantimonate, 4-(2-chloro-4-(4-methylbenzoyl)phenylthio)phenyl diphenylsulfonium hexafluoroantimonate, 4-(2-chloro-4-(4-fluorobenzoyl)phenylthio)phenyl diphenylsulfonium hexafluoroantimonate, 4-(2-chloro-4-(4-methoxybenzoyl)phenylthio)phenyl diphenylsulfonium hexafluoroantimonate, 4-(2-chloro-4-dodecanoylphenylthio)phenyl diphenylsulfonium hexafluoroantimonate, 4-(2-chloro-4-acetylphenylthio)phenyl bis(4-fluorophenyl)sulfonium hexafluoroantimonate, 4-(2-chloro-4-(4-methylbenzoyl)phenylthio)phenyl bis(4-fluorophenyl)sulfonium hexafluoroantimonate, 4-(2-chloro-4-(4-fluorobenzoyl)phenylthio)phenyl bis(4-fluorophenyl)sulfonium hexafluoroantimonate, 4-(2-chloro-4-(4-methoxybenzoyl)phenylthio)phenyl bis(4-fluorophenyl)sulfonium hexafluoroantimonate, 4-(2-chloro-4-dodecanoylphenylthio)phenyl bis(4-fluorophenyl)sulfonium hexafluoroantimonate, 4-(2-chloro-4-acetylphenylthio)phenyl bis(4-chlorophenyl)sulfonium hexafluoroantimonate, 4-(2-chloro-4-(4-methylbenzoyl)phenylthio)phenyl bis(4-chlorophenyl)sulfonium hexafluoroantimonate, 4-(2-chloro-4-(4-fluorobenzoyl)phenylthio)phenyl bis(4-chlorophenyl)sulfonium hexafluoroantimonate, 4-(2-chloro-4-(4-methoxybenzoyl)phenylthio)phenyl bis(4-chlorophenyl)sulfonium hexafluoroantimonate, 4-(2-chloro-4-dodecanoylphenylthio)phenyl bis(4-chlorophenyl)sulfonium hexafluoroantimonate, 4-(2-chloro-4-benzoylphenylthio)phenyl diphenylsulfonium hexafluorophosphate, 4-(2-chloro-4-benzoylphenylthio)phenyl diphenylsulfonium tetrafluoroborate, 4-(2-chloro-4-benzoylphenylthio)phenyl diphenylsulfonium perchlorate, 4-(2-chloro-4-benzoylphenylthio)phenyl diphenylsulfonium trifluoromethanesulfonate, 4-(2-chloro-4-benzoylphenylthio)phenyl bis(4-fluorophenyl)sulfonium hexafluorophosphate, 4-(2-chloro-4-benzoylphenylthio)phenyl bis(4-fluorophenyl)sulfonium tetrafluoroborate, 4-(2-chloro-4-benzoylphenylthio)phenyl bis(4-fluorophenyl)sulfonium perchlorate, 4-(2-chloro-4-benzoylphenylthio)phenyl bis(4-fluorophenyl)sulfonium trifluoromethanesulfonate, 4-(2-chloro-4-benzoylphenylthio)phenyl bis(4-fluorophenyl)sulfonium p-toluenesulfonate, 4-(2-chloro-4- benzoylphenylthio)phenyl bis(4-fluorophenyl)sulfonium camphorsulfonate, 4-(2-chloro-4-benzoylphenylthio)phenyl bis(4-fluorophenyl)sulfonium nonafluorobutanesulfonate, 4-(2-chloro-4-benzoylphenylthio)phenyl bis(4-chlorophenyl)sulfonium hexafluorophosphate, 4-(2-chloro-4-benzoylphenylthio)phenyl bis(4-chlorophenyl)sulfonium tetrafluoroborate, 4-(2-chloro-4-benzoylphenylthio)phenyl bis(4-chlorophenyl)sulfonium perchlorate, 4-(2-chloro-4-benzoylphenylthio)phenyl bis(4-chlorophenyl)sulfonium trifluoromethanesulfonate, diphenyl[4-(phenylthio)phenyl]sulfonium trifluorotrispentafluoroethylphosphate, diphenyl[4-(p-terphenylthio)phenyl]sulfonium hexafluoroantimonate, diphenyl[4-(p-terphenylthio)phenyl]sulfonium trifluorotrispentafluoroethylphosphate, and the like. Among these compounds, 4-(2-chloro-4-benzoylphenylthio)phenyl bis(4-fluorophenyl)sulfonium hexafluoroantimonate (manufactured by ADEKA CORPORATION, ADEKA OPTOMER SP-172), diphenyl[4-(phenylthio)phenyl]sulfonium trifluorotrispentafluoroethylphosphate (manufactured by San-Apro Ltd., CPI-210S), diphenyl[4-(p-terphenylthio)phenyl]sulfonium hexafluoroantimonate, and diphenyl[4-(p-terphenylthio)phenyl]sulfonium trifluorotrispentafluoroethylphosphate (manufactured by San-Apro Ltd., HS-1PG) are preferable.

The content of the cationic polymerization initiator in the curable resin composition is preferably 0.1% to 10% by mass, and more preferably 0.5% to 5% by mass. It is preferable that the content of the cationic polymerization initiator in the curable resin composition is equal to or greater than 0.1% by mass, because then the time required for curing the curable resin composition by active energy ray exposure can be appropriate. Furthermore, it is preferable that the content of the cationic polymerization initiator in the curable resin composition is equal to or smaller than 10% by mass, because then the developability after the exposure using active energy rays can be excellent. The aforementioned content is a value determined on the assumption that the curable resin composition does not contain solvent components which will be described later. Therefore, in a case where the curable resin composition contains solvent components which will be described later, the content of the cationic polymerization initiator from which the mass of the solvent component is excluded just needs to be within the aforementioned range.

Those skilled in the related art understand that other details of the curable resin composition can be embodied based on the methods known to those skilled in the related art described in Japanese Unexamined Patent Application, First Publication No. 2008-180877, Japanese Unexamined Patent Application, First Publication No. 2011-111588, and the like.

In order to form the accumulation portions 13 in the second substrate 20, for example, the substrate body 21 may be covered with the layer 21a having an affinity with secretions (see FIG. 5). Examples of the layer 21a include a layer having undergone a surface treatment by using a surface modifier, a surfactant, and the like. Examples of the surface modifier include a silane coupling agent.

In a case where a protein or a peptide is used as the accumulation portions 13, examples of the layer 21a include a layer treated with aminopropyl triethoxysilane or the like such that an amino group is introduced into the surface thereof.

In a case where cells such as cells stably expressing a membrane protein and the like are used as the accumulation portions 13, examples of the layer 21a include a layer obtained by coating the substrate body 21 with a biomolecule such as polylysine, collagen, fibronectin, or laminin.

Second Embodiment

The structure of the present embodiment is a structure including a first substrate and a second substrate which is disposed to face one side of the first substrate and can include a first cell secreting secretions, in which the first substrate has a plurality of depressions which are open to the other side of the first substrate and each of which has a size that enables each of the depressions to capture one unit of a second cell, at least some of the depressions have communication holes which communicate with one side and the other side of the first substrate and each of which has a size that enables the secretions secreted from the first cell to move through each of the communication holes, and the second cell is a cell responding to the secretions secreted by the first cell.

The constitution of the structure of the present embodiment is the same as that of the structure 1 of the first embodiment, except that the accumulation portions 13 in the structure 1 of the first embodiment are changed to the first cell secreting secretions. The embodiments (for example, the type of secretions and the like) adopted at the time of using the structure of the present embodiment are the same as those of the structure 1 of the first embodiment except for the aforementioned point.

The second cell is not particularly limited as long as it responds to the secretions secreted from the first cell. Examples of the second cell include animal cells (for example, cells derived from a human being, a mouse, a camel, a monkey, a bird, and the like); plant cells; insect cells; fungi such as yeast; bacteria such as *E. coli*; and the like.

Examples of the second cell also include an expression strain obtained by introducing a gene, which encodes a receptor protein binding to a secretory protein, to the aforementioned cells.

In the present invention, among the aforementioned cells, animal cells are preferable. As the animal cells, cells that experience transformation, differentiation, growth, and the like depending on the secretions from other cells are preferable. For example, in a case where the secretions are differentiation factors, and the transformation or differentiation of the cells can depend on the differentiation factors, examples of the cells may include iPS cells and ES cells.

The first cell is not particularly limited as long as it secretes secretions. Examples of the first cell include animal cells (for example, cells derived from a human being, a mouse, a camel, a monkey, a bird, and the like); plant cells; insect cells; fungi such as yeast; bacteria such as *E. coli*; and the like, just like the second cell.

In a case where a cell having a differentiation capacity (for example, an iPS cell, an ES cell, a mesenchymal stem cell, a stem cell derived from a biological body, or a cell obtained by modifying these cells by genetic engineering) is used as the second cell, it is preferable that the first cell is a feeder cell (for example, a fibroblast derived from a mouse fetus, a JK1 cell, an SNL 76/7 cell, or a cell obtained by modifying these cells by genetic engineering).

In the present embodiment, the first substrate and the second substrate are filled with the same liquid, and the liquid flows to the second substrate from the first substrate or to the first substrate from the second substrate through communication holes. While the liquid is flowing, a substance (for example, secretions) in the liquid travels between the first substrate and the second substrate.

The secretions are not particularly limited as long as they have a function acting on the second cell. Examples of the secretions are the same as those exemplified above in the first embodiment.

The structure of the present embodiment adopts a constitution in which the secretions having a predetermined size selectively travel between the first substrate and the second substrate. Therefore, for example, in a case where the second cell is metabolized, the contamination of the first cell may not occur.

Structure-Manufacturing Method

Third Embodiment

The structure-manufacturing method of the present embodiment includes a step 1 of forming a first curable resin film by coating a first support with a first curable resin composition so as to obtain a second substrate, a step 2 of forming a soluble underlayer film on a second support, coating the underlayer film with a second curable resin composition so as to form a second curable resin film, and patterning communication holes on the second curable resin film so as to obtain a supporting layer having patterned communication holes, a step 3 of coating the supporting layer with a third curable resin composition so as to form a third curable resin film and patterning depressions on the third curable resin film so as to obtain a first substrate having patterned depressions, a step 4 of peeling the first substrate from the second support by dissolving the underlayer film, and a step 5 of bonding the first substrate and the second substrate to each other.

<Step 1>

Figure 6:
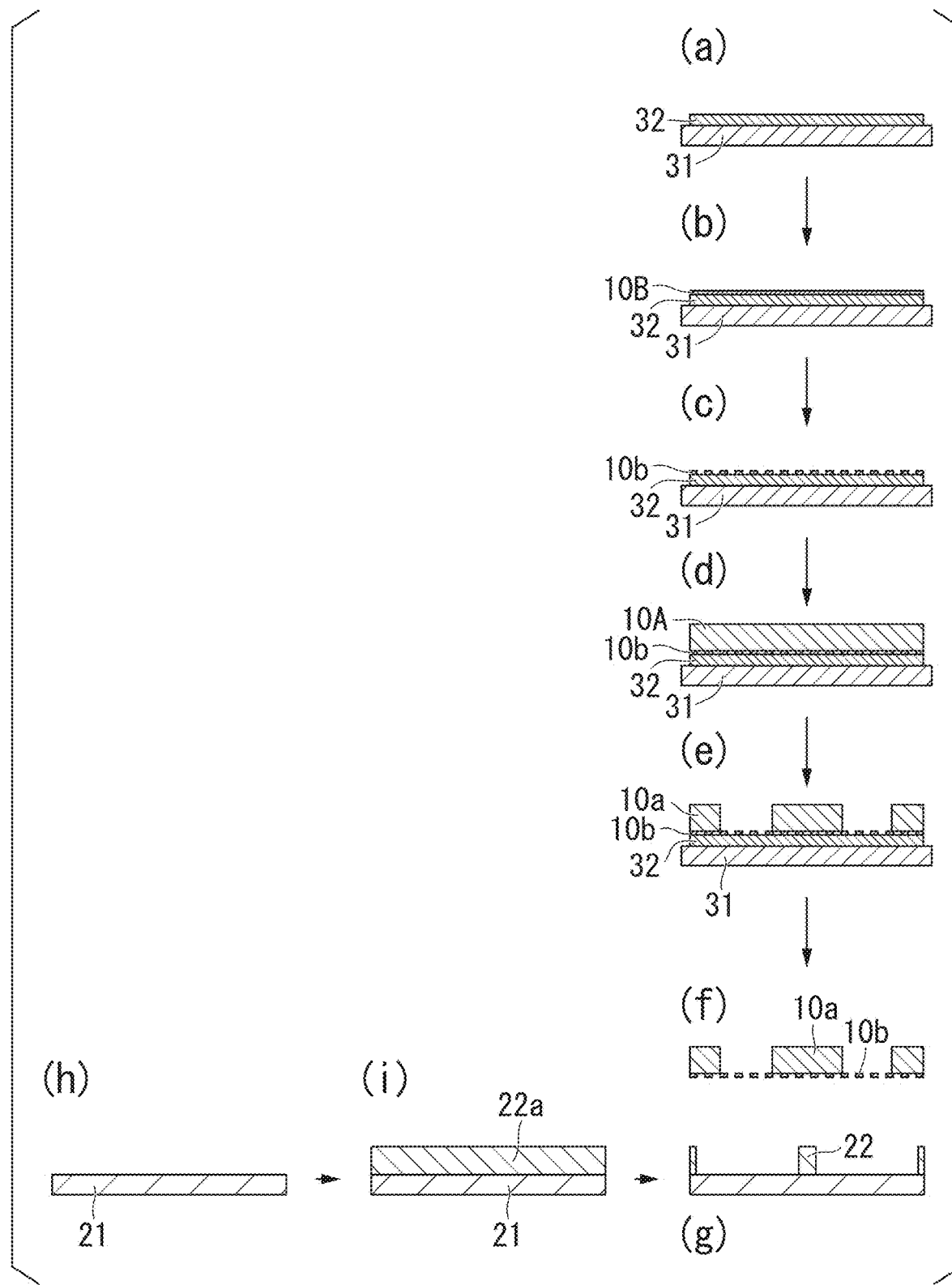
FIG. 6 is a view illustrating steps of an embodiment of a structure-manufacturing method of the present invention.

In this step, for example, as shown in (i) of FIG. 6, a first curable resin film 22a is formed by coating a first support 21 with a first curable resin composition, and development is conducted by performing exposure on the first curable resin film 22a. In this way, a pillar pattern 22 shown in FIG. 6(g) is formed.

In a case where the structure has means for supporting the first substrate, the step of forming the pillar pattern 22 may not be performed. Furthermore, the method for curing the first curable resin composition does not need to be exposure, and known methods can be adopted.

As the support 21, for example, a substrate for electronic parts can be used. From the viewpoint of cell observation, a transparent substrate is preferable. Specifically, it is preferable to adopt a glass substrate.

Examples of the first curable resin composition include the aforementioned curable (photosensitive) resin composition.

It is preferable that a $SiO_2$ film is formed on the entire surface of the second substrate such that cells or proteins in the covering layer are immobilized. The entire surface of the second substrate includes the surface of the pillar pattern 22 and the surface of the support 21 as shown in FIG. 6(g). Examples of the method for forming the $SiO_2$ film include a method of treating the entire surface of the second substrate with tetraisocyanate silane.

<Step 2>

In this step, for example, as shown in FIG. 6(a), a soluble underlayer film 32 is formed on a second support 31, a second curable resin film 10B is formed by coating the underlayer film 32 with a second curable resin composition, and the second curable resin film 10B is subjected exposure and then developed. In this way, a supporting layer 10b having patterned communication holes shown in FIG. 6(c) is formed.

The method for patterning the communication holes is not limited to exposure and development, and it is possible to adopt an imprinting method, a method using a directed self assembly (DSA) technique, and the like. Furthermore, the method for curing the second curable resin composition does not need to be exposure, and known methods can be adopted.

Examples of the second support include a substrate for electronic parts, a substrate for electronic parts in which a predetermined wiring pattern is formed, and the like. More specifically, examples of the second support include a silicon wafer, a substrate made of a metal such as copper, chromium, iron, or aluminum, a glass substrate, and the like. As the material of the wiring pattern, for example, copper, aluminum, nickel, gold, and the like can be used. Examples of the second curable resin composition include the aforementioned curable (photosensitive) resin composition.

In the underlayer film, a polyvinyl alcohol resin, dextrin, gelatin, glue, casein, shellac, gum Arabic, starch, a protein, polyacrylic acid amide, sodium polyacrylate, polyvinyl methyl ether, a styrene-based elastomer, a copolymer of methyl vinyl ether and maleic anhydride, a copolymer of vinyl acetate and itaconic acid, polyvinyl pyrrolidone, acetyl cellulose, hydroxyethyl cellulose, sodium alginate, and the like can be used. These materials may be combined with a plurality of materials soluble in the same type of liquid. From the viewpoint of hardness and flexibility of the underlayer film, the material of the underlayer film may include, for example, a rubber component such as mannan, xanthan gum, or guar gum.

<Step 3>

In this step, for example, as shown in FIG. 6(d), a third curable resin film 10A is formed by coating the supporting layer 10b with a third curable resin composition, and the third curable resin film 10A is subjected to exposure and then to development. In this way, a first substrate is obtained in which depressions are patterned on the supporting layer 10b. Examples of the third curable resin composition include the aforementioned curable (photosensitive) resin composition.

The method for patterning the depressions is not limited to exposure and development, and it is possible to adopt an imprinting method, a method using a directed self assembly (DSA) technique, and the like. The method for curing the third curable resin composition does not need to be exposure, and known methods can be adopted.

<Step 4>

In this step, for example, each substrate is immersed, for example, in a remover (for example, 1-methyl-4-isopropylcyclohexane (p-menthane)) such that the underlayer film is dissolved, thereby peeling the first substrate 10 from the second support 31.

<Step 5>

In this step, for example, the first substrate shown in FIG. 6(f) and the second substrate shown in FIG. 6(g) that are obtained through the steps described above are bonded to each other. At the time of bonding, the supporting layer 10b is bonded to the top of the pillars 22 such that the supporting layer 10b faces the second substrate side. For bonding, the aforementioned curable resin composition may be used as an adhesive.

<<Cell-Sorting Method>>

The cell-sorting method of the present invention is a method for sorting a target cell secreting secretions from a plurality of cells. The cell-sorting method includes a step A of dispersing cells in a first substrate and causing the cell to be captured in depressions, the first substrate including a plurality of depressions each of which has a size that enables each of the depressions to capture one unit of a cell (preferably, one cell) and in which at least some of the depressions have communication holes which communicate with one side and the other side of the first substrate and each of which has a size that enables secretions secreted from the cells to move through each of the communication holes, a step B of causing the cells to secrete the secretions, moving the secretions through the communication holes, and accumulating the secretions moving through the communication holes in accumulation portion of a second substrate, a step C of performing detection of a change that occurs in the accumulation portion, and a step D of identifying target a cell by using a result of the detection as an indicator.

In some cases, the method described above may further include a step E of collecting the target cell. The collected cell can be cultured by the method known to those skilled in the related art, and can also be used in an evaluation system, a secretion production system, and the like according to the method known to those skilled in the related art.

The aforementioned method may further include a step F1 of producing secretions by culturing the target cell or a step F2 of producing secretions by cloning a polynucleotide encoding the secretions in the target cell and culturing another host cell such that the polynucleotide is expressed. In the step F2, the secretions may be produced by further modifying the cloned polynucleotide and then culturing another host cell such that the modified polynucleotide is expressed.

Hereinafter, preferable embodiments of the cell-sorting method of the present invention will be described.

Fourth Embodiment

The cell-sorting method of the present embodiment is a method for sorting a target antibody-producing cell secreting antibodies, which bind specifically to specific antigens, from a plurality of antibody-producing cells. The cell-sorting method includes a step A of dispersing the antibody-producing cells in a first substrate and causing the antibody-producing cells to be captured in depressions, the first substrate including a plurality of depressions each of which has a size that enables each of the depressions to capture one unit of antibody-producing cell (preferably one cell) and in which at least some of the depressions have communication holes which communicate with one side and the other side of the first substrate and each of which has a size that enables the antibodies secreted from the antibody-producing cells to move through each of the communication holes, a step B of causing the antibody-producing cells to secrete the antibodies, moving the antibodies through the communication holes, and accumulating the antibodies moving through the communication holes in accumulation portions of a second substrate, a step of C of performing detection of a change that occurs in the accumulation portions, and a step D of identifying a target antibody-producing cell by using a result of the detection as an indicator.

In some cases, the cell-sorting method of the present embodiment may include a step E of collecting the target antibody-producing cell. Furthermore, the cell-sorting method may further include a step F1 of producing antibodies by culturing the target cell or a step F2 of producing antibodies by cloning a polynucleotide encoding the antibodies in the target cell and culturing another host cell such that the antibodies are expressed. In the step F2, modified antibodies may be produced by further modifying the cloned polynucleotide and then culturing another host cell such that the modified polynucleotide is expressed.

<Step A>

Figure 7:
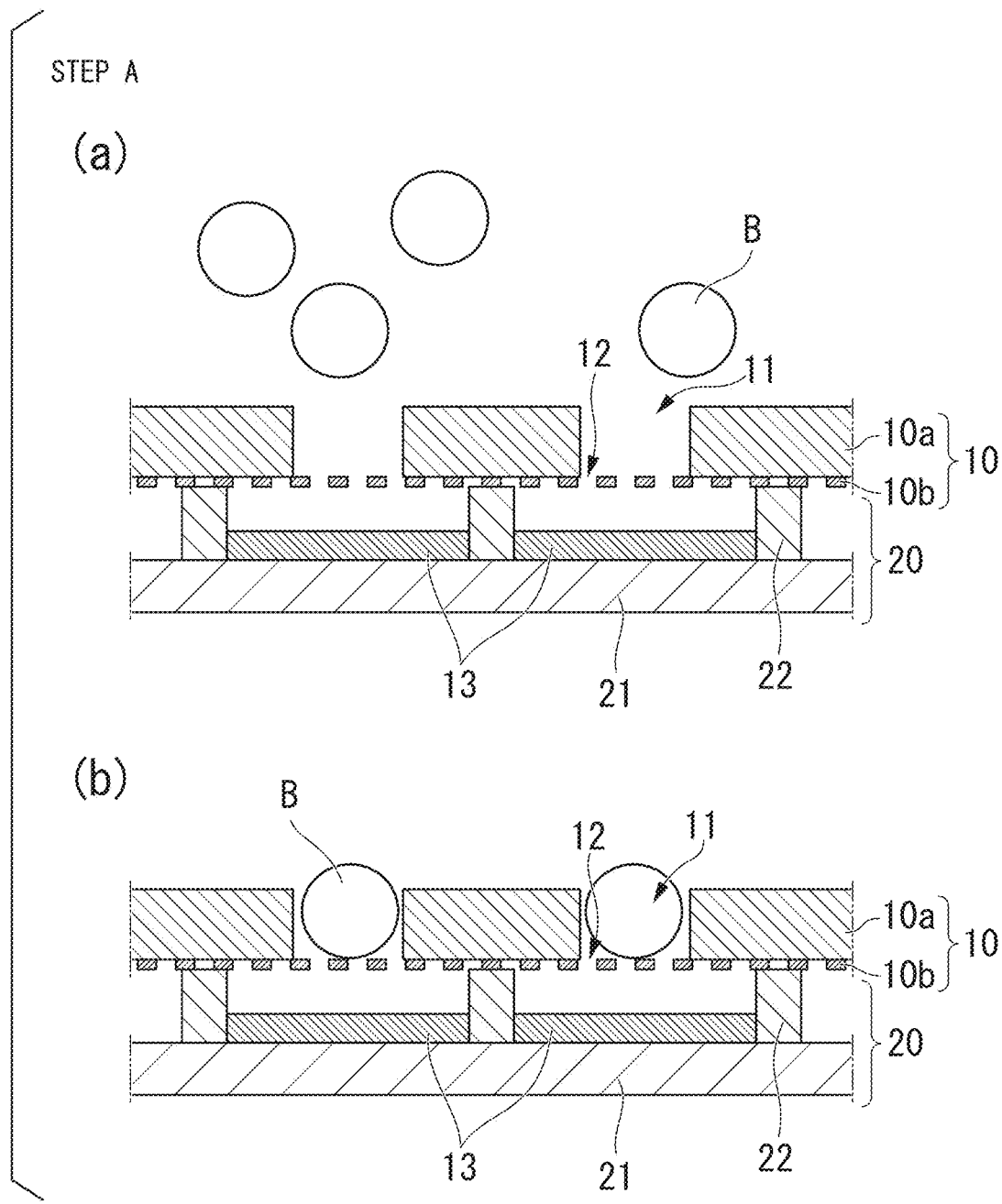
FIG. 7 is a view illustrating a step of an embodiment of a cell-sorting method of the present invention.
Figure 8:
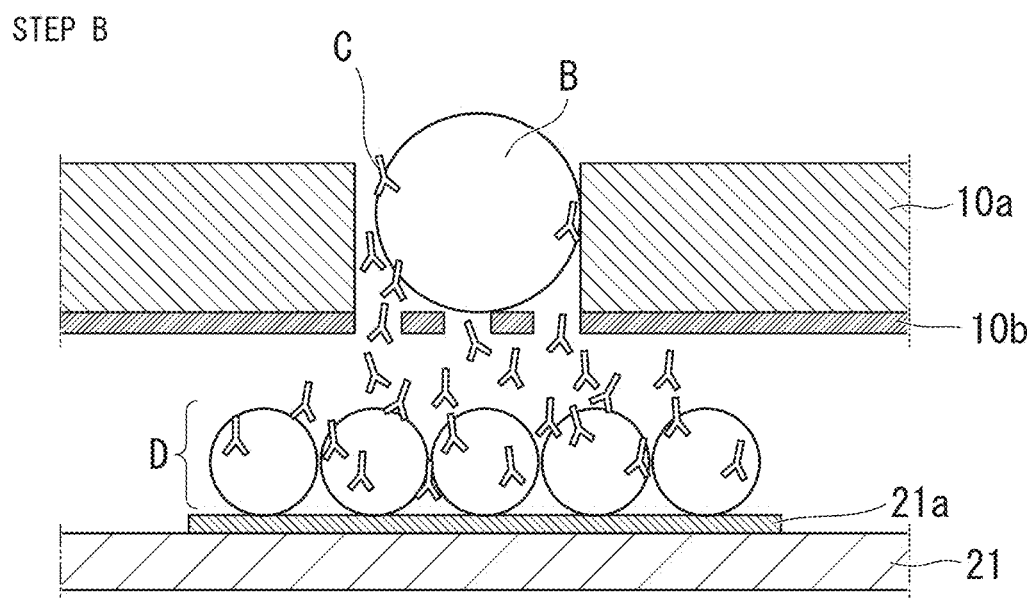
FIG. 8 is a view illustrating a step of an embodiment of the cell-sorting method of the present invention.

The step A is a step of dispersing antibody-producing cells in the first substrate 10 and causing the antibody-producing cells to be captured in depressions, the first substrate 10 including a plurality of depressions each of which has a size that enables each of the depressions to capture one unit of antibody-producing cell (preferably one cell) and in which at least some of the depressions have communication holes which communicate with one side and the other side of the first substrate and each of which has a size that enables the antibodies secreted from the antibody-producing cells to move through each of the communication holes (see FIG. 7).

For example, from the spleen, the lymph node, the bone marrow, and the blood extracted from a mouse, a rat, or a rabbit immunized with antigens, antibody-producing cells are separated. The separated antibody-producing cells are suspended in a medium, and the obtained suspension is seeded in the first substrate 10 of the structure 1 (see FIG. 7(a)). Examples of the used medium include a MEM medium and an RPMI medium. Each of the seeded cells is captured in each of the depressions (see FIG. 7(b)). After the cells are captured in the depressions, it is preferable to wash the first substrate 10 such that the uncaptured antibody-producing cells are removed. It is preferable that the antibody-producing cells to be captured in the depressions are stimulated in advance by using antigens or cytokines such that the cells can produce antibodies which are immunoglobulins.

<Step B>

The step B is a step of causing the antibody-producing cells to secrete antibodies, moving the antibodies through the communication holes, and accumulating the antibodies moving through the communication holes in the accumulation portions of the second substrate. In the present embodiment, it is preferable that the accumulation portions include a first affinity substance having affinity with the antibodies.

Examples of the first affinity substance having affinity with antibodies include antigens or anti-immunoglobulin antibodies that can react with antibodies (immunoglobulins) against the antigens. As the first affinity substance, antigens, particularly, peptide antigens are preferable because these are easily manufactured. For example, the accumulation portions are easily formed by the methods known in the related art, such as a method of forming a layer, which is prepared by modifying an active ester or epoxide, as the layer 21a on the substrate body 21 and immobilizing the peptide through an amino group.

In a case where antibodies against a membrane protein such as GPCR are prepared, each of the accumulation portions including the first affinity substance is preferably a layer including membrane protein-expressing cells obtained by introducing a gene encoding the membrane protein into cells, and more preferably a layer formed of membrane protein-expressing cells. Owing to their properties, some of the membrane proteins are not easily solubilized and are not easily prepared in a state of maintaining the structure thereof. However, in a case where the membrane proteins are expressed on the cell membrane of cultured cells, the membrane proteins can be stably expressed. Therefore, it is preferable that the cultured cells expressing the membrane proteins on the surface of the cell membrane are used as the layer containing the first affinity substance.

In the present embodiment, the first substrate and the second substrate are filled with the same liquid, and the liquid flows to the second substrate from the first substrate or to the first substrate from the second substrate through the communication holes. While the liquid is flowing, the antibodies in the liquid secreted from the antibody-producing cells move to the second substrate 20 through the communication holes included in the depressions. The antibodies having moved come into contact with the first affinity substance in the accumulation portions, and hence a complex of antibody-first affinity substance is formed.

<Step C>

Figure 9:
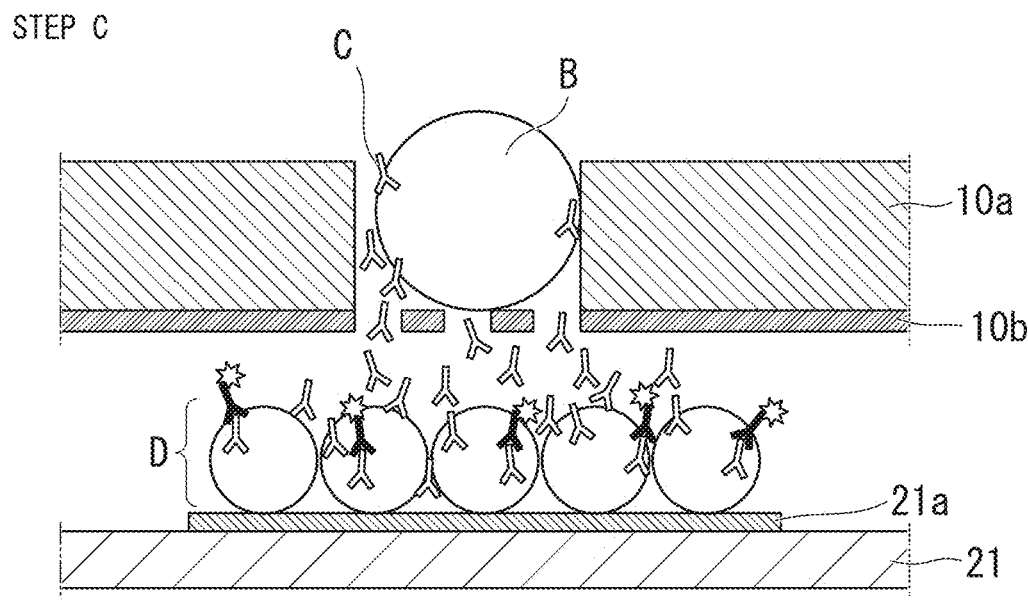
FIG. 9 is a view illustrating a step of an embodiment of the cell-sorting method of the present invention.

The step C is a step of performing detection of a change that occurs in the accumulation portions. The step C is preferably a step of labeling the complex of antibody-first affinity substance with a labeling substance and detecting a signal intensity of the labeling substance in the complex of antibody-first affinity substance (see FIG. 9).

From the viewpoint of specifically detecting the complex of antibody-first affinity substance, in the step C, it is preferable to use a labeled second affinity substance having an antibody recognition site different from an antibody recognition site of the first affinity substance.

In a case where an antigen is used as the first affinity substance, as the second affinity substance, a labeled secondary antibody specific to the Fc portion of IgG is preferable.

Examples of the label include enzymatic labels such as Horse Radish Peroxidase (HRP) and Alkaline Phosphatase (AP). In a case where a chemiluminescent substrate is used for enzymatic labeling, chemiluminescence occurs due to an enzymatic reaction.

Examples of the label include fluorescent labels such as carboxyfluorescein (FAM), 6-carboxy-4',5'-dichloro-2',7'-dimethoxyfluorescein (JOE), fluorescein isothiocyanate (FITC), tetrachlorofluorescein (TET), 5'-hexachloro-fluorescein-CE phosphoramidite (HEX), Cy3, Cy5, Alexa 568, and Alexa 488. In a case where the labeled second affinity substance binds to the complex of antibody-first affinity substance and a complex is formed, the complex emits predetermined fluorescent light.

<Step D>

The step D is a step of identifying a target antibody-producing cell by using a result of the detection as an indicator and preferably by using the signal intensity of the labeling substance as an indicator.

In the present embodiment, the target antibody-producing cell is an antibody-producing cell secreting antibodies binding specifically to specific antigens.

The specificity of the antibodies produced from the antibody-producing cell depends on a degree of formation of the complex of antibody-first affinity substance, that is, on the signal intensity of the complex of antibody-first affinity substance labeled in the step C.

In the second substrate 20, the cell present in the depression corresponding to the site showing a high signal intensity is the target antibody-producing cell.

<Step E>

Figure 10:
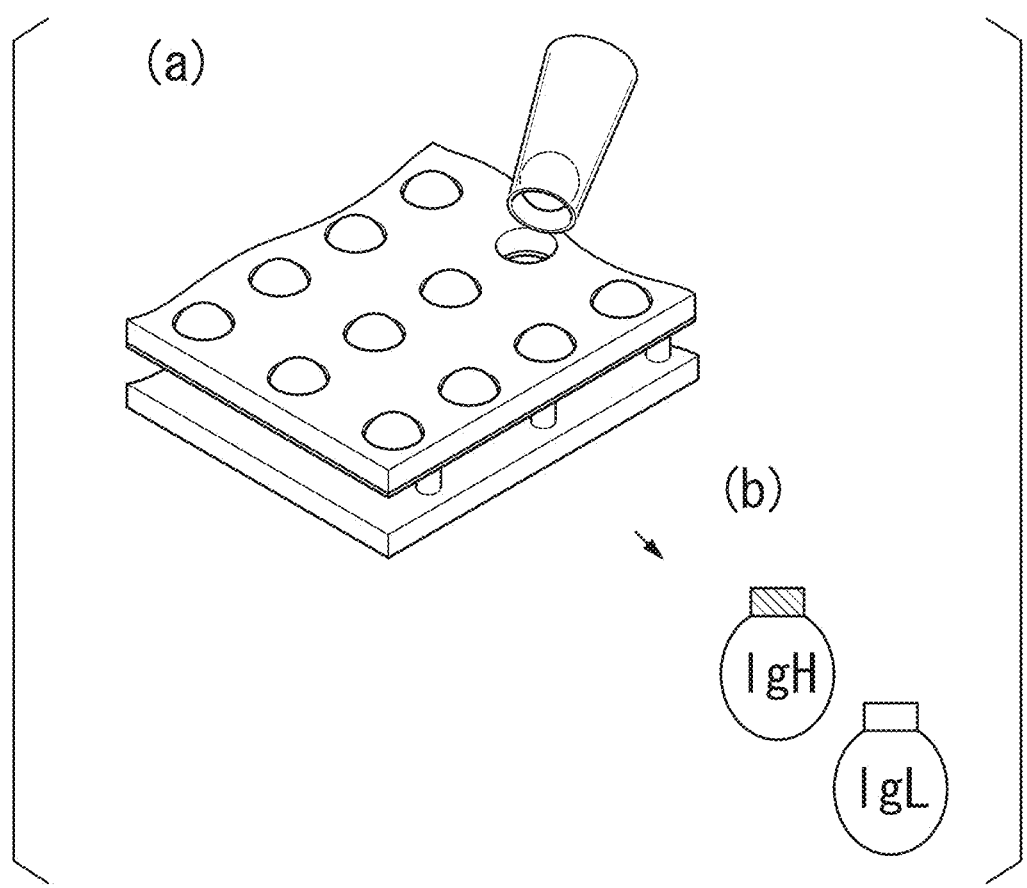
FIG. 10 is a view illustrating a step of an embodiment of the cell-sorting method of the present invention.

The step E is a step of collecting the target antibody-producing cell, and is preferably a step of collecting the target antibody-producing cell by using the signal intensity of the aforementioned labeling substance as an indicator (see FIG. 10). The cell is collected using a manipulator, a pipette, or the like (see FIG. 10(a)).

<Step F1 or Step F2>

The step F1 is a step of producing antibodies by culturing the target cell. As the cell used in the step F1, a hybridoma is preferable. Because a hybridoma grows while producing antibodies, a large amount of target antibodies can be obtained.

The step F2 is a step of producing antibodies by cloning a polynucleotide encoding the antibodies in the target cell and culturing another host cell such that the antibodies are expressed. After the target antibody-producing cell is cultured, by RT-PCR or the like, the polynucleotide encoding the antibodies can be cloned (see FIG. 10(b)). In some cases, the polynucleotide encoding the antibodies may be further modified. In addition, by using the polynucleotide encoding the antibodies or the modified polynucleotide, a recombinant vector may be constructed. Moreover, by introducing the constructed recombinant vector into a host cell, a transformant may be constructed. The transformant may be cultured in a medium, the antibodies in the culture may be generated and accumulated, and the aforementioned antibodies may be collected from the culture.

It goes without saying that those skilled in the related art understand that the step F1 or the step F2 can be embodied based on the methods known to those skilled in the related art.

According to the present embodiment, the culture system of the antibody-producing cell of the first substrate and the antibody detection system of the second substrate are separated from each other. Therefore, particularly in an evaluation method in which cultured cells expressing a membrane protein on the surface of the cell membrane are used, it is possible to evaluate the antibody producing capacity of the antibody-producing cell in a simple manner while preventing the antibody-producing cell from being mixed with a cell for evaluation. As a result, the target antibody-producing cell can be rapidly collected.

Hereinafter, the difference in the constitution between the fifth and sixth embodiments and the fourth embodiment will be specifically described.

Fifth Embodiment

The cell-sorting method of the present embodiment is a method for sorting a target polypeptide-producing cell secreting a specific polypeptide from a plurality of polypeptide-producing cells including cytokines, hormones, and the like. The cell-sorting method includes a step A of dispersing polypeptide-producing cells in a first substrate, including a plurality of depressions each of which has a size that enables each of the depressions to capture one unit of polypeptide-producing cell (preferably one cell) and in which at least some of the depressions have communication holes which communicate with one side and the other side of the first substrate and each of which has a size that enables the polypeptide secreted from the polypeptide-producing cells to move through each of the communication holes, and causing the polypeptide-producing cells to be captured in the depressions, a step B of causing the polypeptide-producing cells to secrete the polypeptide, moving the polypeptide through the communication holes, and accumulating the polypeptide moving through the communication holes in accumulation portions of a second substrate, a step C of performing detection of a change that occurs in the accumulation portions, and a step D of identifying a target polypeptide-producing cell by using a result of the detection as an indicator.

In some cases, the cell-sorting method of the present embodiment may include a step E of collecting the target polypeptide-producing cell. Furthermore, the cell-sorting method may further include a step F1 of producing a polypeptide by culturing the target cell or a step F2 of producing a polypeptide by cloning a polynucleotide encoding the polypeptide in the target cell and culturing another host cell such that the polypeptide is expressed. In the step F2, a modified polypeptide may be produced by further modifying the cloned polynucleotide and then culturing another host cell such that the modified polynucleotide is expressed.

<Step A>

The step A is a step of dispersing polypeptide-producing cells in the first substrate 10 and causing the polypeptide-producing cells to be captured in depressions, the first substrate 10 including a plurality of depressions each of which has a size that enables each of the depressions to capture one unit of polypeptide-producing cell (preferably one cell) and in which at least some of the depressions have communication holes which communicate with one side and the other side of the first substrate and each of which has a size that enables the polypeptide secreted from the polypeptide-producing cell to move through each of the communication holes (see FIG. 7).

Examples of the polypeptide include cytokines, hormones, and the like.

<Step B>

The step B is a step of causing the polypeptide-producing cells to secrete the polypeptide, moving the polypeptide through the communication holes, and accumulating the polypeptide moving through the communication holes in accumulation portions of the second substrate.

In the present embodiment, the accumulation portions may include a first affinity substance having affinity with the polypeptide. Examples of the first affinity substance having affinity with cytokines that is used for sorting a cytokine-producing cell include receptors or anti-immunoglobulin antibodies that can react with cytokines. Examples of the first affinity substance having affinity with hormones that is used for sorting a hormone-secreting cell include receptors.

In a case where a receptor is used as the first affinity substance, each of the accumulation portions including the first affinity substance is preferably a layer including cells stably expressing a receptor obtained by introducing a gene encoding the receptor into cells, and more preferably a layer formed of the cells stably expressing a receptor.

The peptide hormone such as a growth hormone transmits signals by binding to a hormone receptor, and activates the transcription of a target gene such that the hormone performs its function. In the present embodiment, the accumulation portions may include reporter gene-introduced cells responding to a polypeptide which is a hormone.

In sorting the hormone-secreting cell, the reporter gene-introduced cell responding to a hormone exploits the aforementioned activation of transcription. Such a cell is obtained by stably introducing a molecule, which is prepared by combining a hormone response element with a transcriptional regulatory region of a reporter gene, into a cell which endogenously or exogenously highly expresses a hormone receptor.

Examples of the reporter gene include genes encoding a fluorescent protein such as GFP or enzymes such as luciferase, β-galactosidase, and β lactamase.

<Step C>

The step C is a step of performing detection of a change that occurs in the accumulation portions.

In sorting the cytokine-producing cell, the step C is preferably a step of labeling a complex of cytokine-first affinity substance with a labeling substance and detecting the signal intensity of the labeling substance in the complex of cytokine-first affinity substance or detecting whether or not a signal is present.

In sorting the hormone-secreting cell, the step C is preferably a step of detecting the intensity of light or fluorescence emitted from the reporter gene-introduced cell responding to hormones or detecting whether or not light or fluorescence is emitted from the reporter gene-introduced cell. Alternatively, the step C is preferably a step of labeling a complex of hormone-hormone receptor with a labeling substance and detecting the intensity of the labeling substance in the complex of hormone-hormone receptor or detecting whether or not the labeling substance is present.

<Step D>

The step D is a step of identifying the target polypeptide-producing cell by using a result of the detection as an indicator and preferably by using the signal intensity of the labeling substance as an indicator.

The specificity of the polypeptide produced by the polypeptide-producing cell depends on the signal intensity of the complex of polypeptide-first affinity substance labeled in the step C, the signal intensity from the reporter gene-introduced cell responding to the polypeptide, and the like.

In the second substrate 20, a cell present in a depression corresponding to the site showing a high signal intensity is the target polypeptide-producing cell.

<Step E>

The step E is a step of collecting the target polypeptide-producing cell, and is preferably a step of collecting the target polypeptide-producing cell by using the signal intensity of the aforementioned labeling substance as an indicator (see FIG. 10). The cell is collected using a manipulator, a pipette, and the like (see FIG. 10(a)).

<Step F1 or Step F2>

The step F1 is a step of producing a polypeptide by culturing the target cell. Examples of polypeptide, cytokine, hormone, and cells used in the step F1 include the cytokine-producing cells or the hormone-secreting cells described above.

The step F2 is a step of producing a polypeptide by cloning a polynucleotide encoding the aforementioned polypeptide in the target cell and culturing another host cell such that the polypeptide is expressed. After the target polypeptide-producing cell is cultured, by RT-PCR or the like, the polynucleotide encoding the target polypeptide can be cloned (see FIG. 10(b)). In some cases, the polynucleotide encoding the polypeptide can be further modified. Furthermore, by using the polynucleotide encoding the polypeptide or the modified polynucleotide, a recombinant vector may be constructed. In addition, a transformant may be constructed by introducing the constructed recombinant vector into a host cell. The transformant may be cultured in a medium, the polypeptide may be generated and accumulated in the culture, and the polypeptide may be collected from the culture.

It goes without saying that those skilled in the related art can understand that the step F1 or the step F2 can be embodied based on the methods known to those skilled in the related art.

Cytokines are known to function as vaccines in various diseases including infectious diseases, cancer, allergy, and autoimmune diseases through specific immune responses.

In the present embodiment, the sorting of a cytokine-producing cell secreting a cytokine binding to a specific receptor and the analysis of the cytokine can help the development of a novel vaccine.

Furthermore, at the time of mass-producing a cytokine such as interferon used as a pharmaceutical product, the cell-sorting method of the present embodiment is useful. Specifically, by sorting an interferon-producing cell by using the cell-sorting method of the present embodiment and causing the interferon-producing cells to secrete a large amount of interferon, a vaccine can be efficiently produced.

In addition, the present embodiment is suitably used for sorting cells secreting specific hormones. For example, the present embodiment is suitably used for sorting a cell group into which a gene modification library encoding hormones is introduced. According to the present embodiment, a hormone receptor activation ability of a modified hormone can be evaluated in a simple manner. Therefore, it is possible to rapidly sort a hormone that inhibits or activates the hormone receptor.

Sixth Embodiment

The cell-sorting method of the present embodiment is a method for sorting a target secretion-producing cell having a high secretion-producing ability from a plurality of secretion-producing cells. The cell-sorting method includes a step A of dispersing secretion-producing cells in a first substrate, including a plurality of depressions each of which has a size that enables each of the depressions to capture one unit of secretion-producing cell (preferably one cell) and in which at least some of the depressions have communication holes which communicate with one side and the other side of the first substrate and each of which has a size that enables the secretions secreted from the secretion-producing cells to move through each of the communication holes, and causing the secretion-producing cells to be captured in the depressions, a step B of causing the secretion-producing cells to secrete the secretions, moving the secretions through the communication holes, and accumulating the secretions having moved through the communication holes in accumulation portions of a second substrate, a step C of performing detection of a change that occurs in the accumulation portions, and a step D of identifying a target secretion-producing cell having a high secretion-producing ability by using a result of the detection as an indicator.

In some cases, the cell-sorting method of the present embodiment may include a step E of collecting the target secretion-producing cell. Furthermore, in some cases, the cell-sorting method of the present embodiment may include a step F1 of producing secretions by collecting and culturing the target secretion-producing cell or a step F2 of producing secretions by cloning a polynucleotide encoding the secretions in the target cell and culturing another host cell such that the polynucleotide is expressed. In the step F2, antibodies may be produced by modifying the cloned polynucleotide and then culturing another host cell such that the modified polynucleotide is expressed.

<Step A>

The step A is a step of dispersing secretion-producing cells in the first substrate 10 and causing the secretion-producing cells to be captured in depressions, the first substrate 10 including a plurality of depressions each of which has a size that enables each of the depressions to capture one unit of secretion-producing cell (preferably one cell) and in which at least some of the depressions have communication holes which communicate with one side and the other side of the first substrate and each of which has a size that enables the secretions secreted from the secretion-producing cells to move through each of the communication holes (see FIG. 7).

For example, antibody-producing cells are constructed by introducing a heavy-chain antibody gene or a light-chain antibody gene into animal cells such as CHO cells or 293 cells, a suspension is prepared by suspending the antibody-producing cells in a medium, and the suspension is seeded in the first substrate 10 of the structure 1 (see FIG. 7(a)). After the cells are captured in the depressions, it is preferable to wash the first substrate 10 such that uncaptured antibody-producing cells are removed.

<Step B>

The step B is a step of causing the secretion-producing cells to secrete secretions, moving the secretions through the communication holes, and accumulating the secretions moving through the communication holes in accumulation portions of a second substrate.

In the present embodiment, the accumulation portions include a first affinity substance having affinity with the secretions.

In a case where the secretions are antibody molecules, examples of the first affinity substance having affinity with the antibodies include antigens or anti-immunoglobulin antibodies that can react with the antibodies (immunoglobulin), protein A, protein G, and protein L. Among these, anti-immunoglobulin antibodies, protein A, protein G, and protein L are preferable, because these can be widely used regardless of the antigens. For example, the accumulation portions can be easily formed by the methods known in the related art, such as a method of forming a layer, which is obtained by modifying an active ester or epoxide, as the layer 21a on the second substrate 21 and immobilizing a peptide through an amino group.

In the present embodiment, the first substrate and the second substrate are filled with the same liquid. Through the communication holes, the liquid flows to the second substrate from the first substrate or to the first substrate from the second substrate. While the liquid is flowing, the secretions in the liquid that are secreted from the secretion-producing cells move to the second substrate 20 through the communication holes included in the depressions. The secretions having moved come into contact with the first affinity substance in the accumulation portions and form a complex of secretion-first affinity substance.

<Step C>

The step C is a step of performing detection of a change that occurs in the accumulation portions. The step C is preferably a step of labeling the complex of secretion-first affinity substance with a labeling substance and detecting a signal intensity of the labeling substance in the complex of secretion-first affinity substance (see FIG. 9). From the viewpoint of specifically detecting the complex of secretion-first affinity substance, in the step C, it is preferable to use a labeled second affinity substance having a secretion recognition site different from a secretion recognition site of the first affinity substance.

In a case where protein A is used as the first affinity substance, the second affinity substance is preferably, but is not limited to, a labeled secondary antibody specific to the Fab portion of IgG. As the secondary antibody, Fab or F(ab')$_2$ is more preferable.

Examples of the label include enzymatic labels such as Horse Radish Peroxidase (HRP) and Alkaline Phosphatase (AP). In a case where a chemiluminescent substrate is used for enzymatic labeling, chemiluminescence occurs due to an enzymatic reaction.

Examples of the label include fluorescent labels such as carboxyfluorescein (FAM), 6-carboxy-4',5'-dichloro 2',7'-dimethoxyfluorescein (JOE), fluorescein isothiocyanate (FITC), tetrachlorofluorescein (TET), 5'-hexachloro-fluorescein-CE phosphoramidite (HEX), Cy3, Cy5, Alexa 568, and Alexa 488. In a case where the fluorescence-labeled second affinity substance binds to the complex of secretion-first affinity substance and a complex is formed, and the complex emits predetermined fluorescent light.

<Step D>

The step D is a step of identifying a target secretion-producing cell having a high secretion-producing ability by using a result of the detection as an indicator. The step D is preferably a step of identifying a target secretion-producing cell having a high secretion-producing ability by using a signal intensity of the labeling substance as an indicator.

In the present embodiment, for example, in a case where the target secretion-producing cell having a high secretion-producing ability is a target antibody-producing cell having a high antibody-producing ability, the target antibody-producing cell means a cell secreting a large amount of antibodies (or a larger number of antibody molecules) per hour.

The antibody-producing ability depends on a degree of formation of the complex of antibody-first affinity substance, that is, on the signal intensity of the complex of antibody-first affinity substance labeled in the step C.

In the second substrate 20, a cell present in a depression corresponding to the site showing a high signal intensity is a target secretion-producing cell having a high secretion-producing ability.

<Step E>

The step E is a step of collecting the target secretion-producing cell. In the step E, a cell present in a depression corresponding to a site showing a high signal intensity in the second substrate 20 may be collected as the target secretion-producing cell. After the cell is collected using a manipulator, a pipette, or the like (see FIG. 10(a)) and cultured, secretions such as antibodies can be manufactured.

<Step F1 or Step F2>

The step F1 is a step of producing secretions by culturing the target cell. In a case where the secretions are antibodies, as the cell used in the step F1, animal cells stably expressing antibodies are preferable which are obtained by introducing a heavy-chain antibody gene or a light-chain antibody gene into animal cells such as CHO cells and 293 cells. The animal cells stably expressing antibodies grow while producing antibodies. Therefore, a large amount of target antibodies are obtained.

The step F2 is a step of breeding or modifying the target cell secreting the secretions. By breeding or gene introduction, other characteristics or traits can be additionally imparted to the target cell. During the gene introduction, a gene that encodes the target secretions may be introduced. Alternatively, a polynucleotide that encodes other proteins or a polynucleotide that expresses non-coding RNA may be introduced. In some cases, sorting starting from the step A can be repeated.

It goes without saying that those skilled in the related art can understand that the step F1 or the step F2 can be embodied based on the methods known to those skilled in the related art.

According to the present embodiment, in the field of biotechnology-applied pharmaceutical products such as antibody medicines, by using cells highly producing a target protein, the pharmaceutical products can be efficiently produced.

In order to produce biotechnology-applied pharmaceutical products, the productive cells are required to have clonality (singularity) (for example, International Council for Harmonization of Technical Requirements for Pharmaceuticals for Human Use (ICH) guideline Q5D). According to the present embodiment, after the introduction of the gene of a target protein or polypeptide, cells highly producing pharmaceutical products derived from one cell can be rapidly isolated. Therefore, the present embodiment is extremely useful for the development of pharmaceutical products.

The entire contents of all of the technical documents cited in the present specification are incorporated into the present specification by reference.

The terms used in the present specification are used for describing specific embodiments and should not be interpreted as terms limiting the invention. The terms (including technical terms and scientific terms) used in the present specification should be interpreted as terms having the same meanings as those widely understood by those skilled in the related art to which the present invention belongs, unless other definitions of the terms are specified in the present specification. Furthermore, the terms used in the present specification should not be interpreted as terms having idealized meanings or excessively formal meanings.

The term "include" used in the present specification means that the described matters (a member, a step, a factor, a number, and the like) are present, except for the case where the context clearly shows that the term should be understood in a different way. The term "include" does not exclude a case where other matters (a member, a step, a factor, a number, and the like) are also present.

The embodiments of the present invention are described with reference to schematic views in some cases, and sometimes the embodiments are exaggeratedly expressed in the views for clear description.

In the present specification and claims, unless otherwise specified and unless inconsistencies are found in the context, an object represented by each noun described in the present specification and claims means that there may be a single object or a plurality of objects.

EXAMPLES

Hereinafter, the present invention will be more specifically described based on examples, but the present invention is not limited to the following examples.

[Manufacturing of Structure]

<Manufacturing of Second Substrate>

A glass substrate was coated with a photosensitive resin composition (see Japanese Unexamined Patent Application, First Publication No. 2008-180877 and Japanese Unexamined Patent Application, First Publication No. 2011-111588) by using a spin coater (1,000 rpm, 20 seconds), followed by pre-baking for 5 minutes at 90° C. by using a hot plate. Then, pattern exposure (soft contact, GHI line, 500 mJ) was performed using a parallel light exposure machine (manufactured by Hakuto Co., Ltd., MAT-2501 model), and post-exposure heating was performed for 5 minutes at 90° C. by using a hot plate. Thereafter, by an immersion method using propylene glycol monomethyl ether acetate (PGMEA), a developing treatment was performed for 2 minutes. Subsequently, for each substrate, the resin pattern obtained after development was post-baked for 1 minute at 120° C. by using an oven, thereby obtaining a resin pattern of a second substrate.

<Manufacturing of First Substrate>

(Patterning of Communication Holes)

A silicon substrate was coated with an underlayer agent by using a spin coater (1,500 rpm, 20 seconds), followed by pre-baking for 1 minute at 90° C. and then for 3 minutes at 120° C. by using a hot plate, thereby forming an underlayer film.

The underlayer film was coated with the aforementioned photosensitive resin composition by using a spin coater (3,000 rpm, 20 seconds), followed by pre-baking for 3 minutes at 90° C. by using a hot plate. Then, pattern exposure (soft contact, I line, 150 mJ) was performed using PLA-501F (contact aligner: manufactured by Canon Inc.), and post-exposure heating was performed for 5 minutes at 90° C. by using a hot plate. Thereafter, by an immersion method using PGMEA, a developing treatment was performed for 30 seconds. Subsequently, for each substrate, the resin pattern obtained after development was post-baked for 1 minute at 120° C. by using an oven, thereby obtaining a resin pattern of communication holes having a palisade shape.

(Patterning of Depressions)

The resin pattern of communication holes obtained as above was coated with the aforementioned photosensitive resin composition by using a spin coater (1,000 rpm, 20 seconds), followed by pre-baking for 5 minutes at 90° C. by using a hot plate. Then, pattern exposure (soft contact, GHI line, 60 mJ) was performed using a parallel light exposure machine (manufactured by Hakuto Co., Ltd., MAT-2501 model), and post-exposure heating was performed for 5 minutes at 90° C. by using a hot plate. Thereafter, by an immersion method using PGMEA, a developing treatment was performed for 2 minutes. Subsequently, for each substrate, the resin pattern obtained after development was post-baked for 1 minute at 120° C. by using an oven, thereby obtaining a depression pattern.

(Peeling of First Substrate)

The first substrate in which the well layer obtained as above was patterned was immersed in a remover such that the underlayer film was dissolved. In this way, the first substrate, in which a well pattern was formed on a microporous resin pattern, was peeled from the silicon substrate.

<Bonding First Substrate and Second Substrate to Each Other>

The entire surface of the resin pattern of the second substrate obtained as above was treated with tetraisocyanate silane. Then, the top of the resin pattern of the second substrate was coated with a substance obtained by coating a silicon wafer with an adhesive, followed by pre-baking for 1 minute at 35° C. Thereafter, the first substrate obtained as above was bonded to the second substrate such that the pattern of communication holes faced down. Subsequently, exposure (soft contact, GHI line, 60 mJ) was performed using a parallel light exposure machine (manufactured by Hakuto Co., Ltd., MAT-2501 model), and post-exposure heating was performed for 3 minutes at 35° C. and then for 1 minute at 90° C. by using a hot plate such that the adhesive was cured, thereby bonding the first substrate and the second substrate to each other.

The thickness of the first substrate was 10 μm, the diameter of each of the depressions was 12 μm, the pitch between the depressions was 100 μm, and the width of the each of the communication holes having a palisade shape was 2 μm. Regarding the size of the structure, the length and width of the structure were 128 mm and 86 mm respectively when seen in a plan view, and the thickness of the structure was 15 mm.

Figure 11:
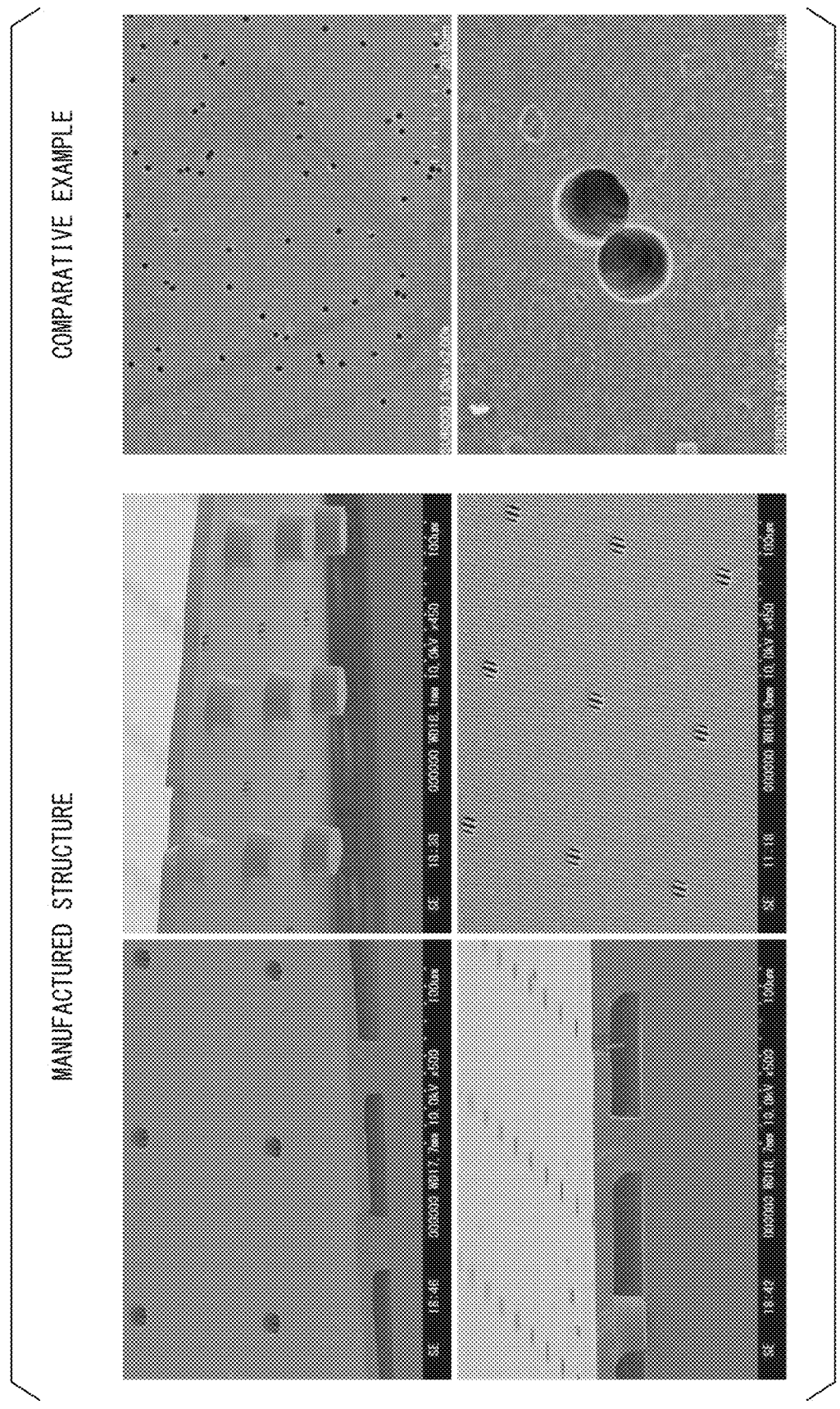
FIG. 11 is a view showing results of examples.

Through the steps described above, a structure could be manufactured which include a first substrate and a second substrate disposed to face one side of the first substrate, in which the first substrate has a plurality of depressions which are open to the other side of the first substrate and each of which has a size that enables each of the depressions to capture one unit of a cell, at least some of the depressions have communication holes which communicate with one side and the other side of the first substrate and each of which has a size that enables secretions secreted from the cell to move through each of the communication holes, the second substrate can include accumulation portions in which the secretions moving through the communication holes are accumulated, and the accumulation portions can correspond to the depressions. FIG. 11 show images of the manufactured structure captured using a scanning electron microscope and images of a transwell having random pores (Merck Millipore, Millicell® 24-Well Cell Culture Insert, pore size; 1 um, film thickness: about 10 μm) as a comparative example.

Example 1

Figure 12:
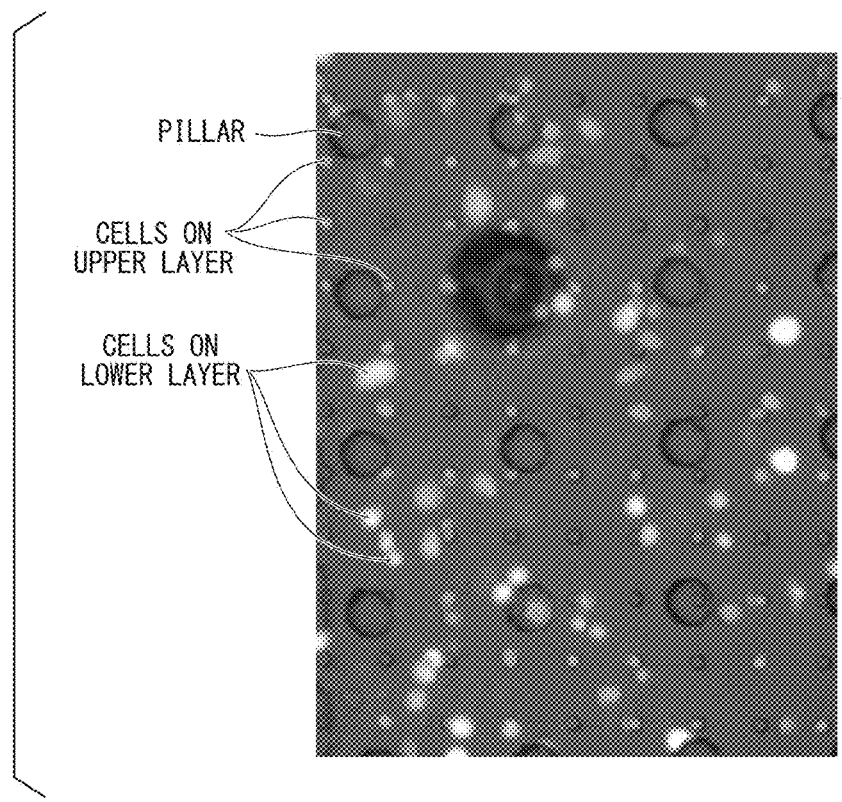
FIG. 12 is a view showing results of examples.

CHO-K1 cells were seeded in the second substrate of the structure manufactured as above and stained with Calcein-AM. Namalwa cells stained in advance with CytoRed were seeded in the first substrate, and the structure was left to stand in a $CO_2$ incubator for 5 minutes. FIG. 12 is a fluorescence image of the structure observed from the first substrate side.

As shown in FIG. 12, it was confirmed that the cells seeded in the first substrate and the cells seeded in the second substrate can be separated from each other.

<Manufacturing of Substrate Only Having Depressions>

A glass substrate was coated with the aforementioned photosensitive resin composition by using a spin coater (1,000 rpm, 20 seconds), followed by pre-baking for 5 minutes at 90° C. by using a hot plate. Then, pattern exposure (soft contact, GHI line, 60 mJ) was performed using a parallel light exposure machine (manufactured by Hakuto Co., Ltd., MAT-2501 model), and post-exposure heating was performed for 5 minutes at 90° C. by using a hot plate. Thereafter, by an immersion method using PGMEA, a developing treatment was performed for 2 minutes. Subsequently, for each substrate, the resin pattern obtained after development was post-baked for 1 minute at 120° C. by using an oven, thereby obtaining a depression pattern.

<Comparing Manufactured Structure with Substrate Only Having Depressions in Terms of Cell Storage Rate>

Figure 13:
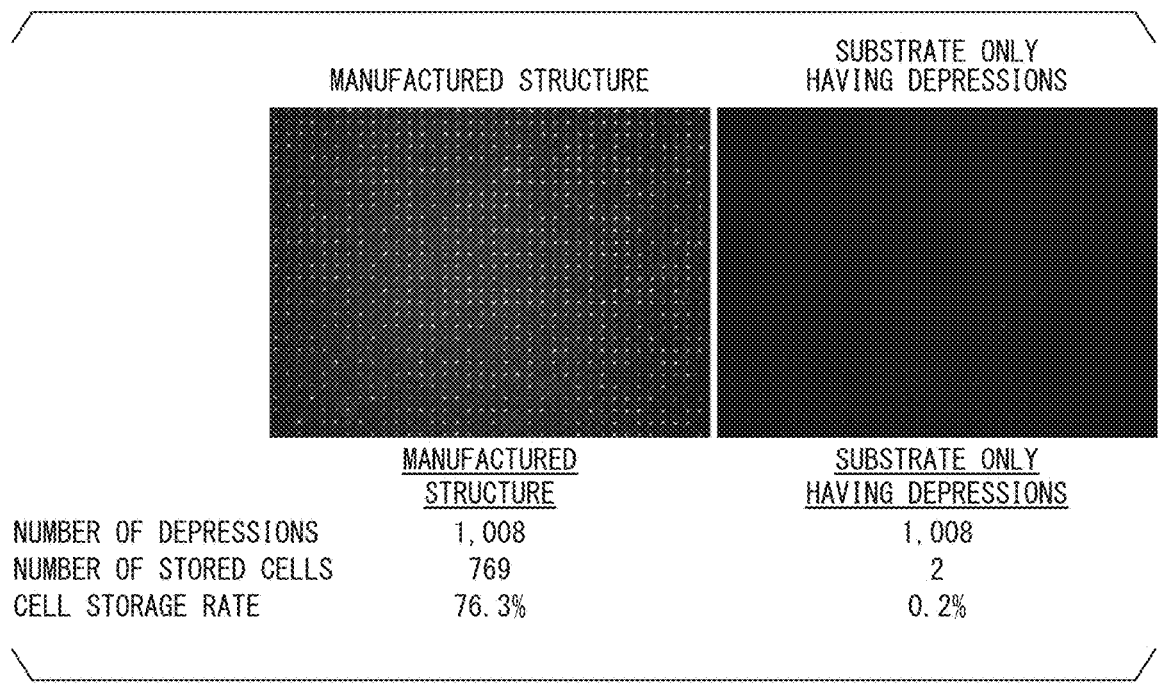
FIG. 13 is a view showing results of examples.

Ba/F3 cells at $4 \times 10^5$ cells/500 μm stained in advance with Calcein-AM were seeded in the structure manufactured as above and in the substrate only having depressions, and the structure and the substrate were left to stand for 3 minutes. The medium was removed using an aspirator such that the cells not being stored in the depressions were removed. The substrate surface was washed by adding a medium thereto, and then the medium was removed using an aspirator. The washing operation was performed three times in total. FIG. 13 shows fluorescence images of the structure observed from the first substrate side after the medium was added. The cell storage rate in the depressions of the manufactured structure was 76.3% while the cell storage rate of the substrate having only depressions was 0.2%. It was confirmed that the cell storage rate of the manufactured structure is high.

Example 2

CHO-DG44 cells stably expressing a membrane protein were seeded in and bonded to the second substrate of the structure manufactured as above, and cultured for 48 hours.

Then, Ba/F3 cells stably expressing mouse anti-membrane protein antibodies that were stained with a PKH26 red fluorescent cell linker Mini Kit (Sigma-Aldrich Co. LLC., MINI 26-IKT) were seeded in the first substrate and arranged in the wells. After the arrangement, the substrate was washed three times such that the Ba/F3 cells not being arranged in the wells were removed. The cells were cultured overnight in a $CO_2$ incubator, and through the communication holes, the mouse anti-membrane protein antibodies secreted from the Ba/F3 cells were caused to react with the CHO-DG44 cells stably expressing a membrane protein that were on the second substrate.

Thereafter, the second substrate was washed three times with an FBS-supplemented RPMI 1640 medium. Alexa 488-labeled goat anti-mouse IgG antibodies (Life Technologies, #A11001) were added to the FBS-supplemented RPMI 1640 medium such that the antibodies were diluted at a ratio of 1/1,000. The Alexa 488-labeled goat anti-mouse IgG antibody-supplemented RPMI 1640 medium was added to the second substrate and caused to react with mouse anti-membrane protein antibodies for 1 hour. The second substrate was washed three times with the FBS-supplemented RPMI 1640 medium and observed with CKX 41 manufactured by OLYMPUS CORPORATION.

Figure 14:
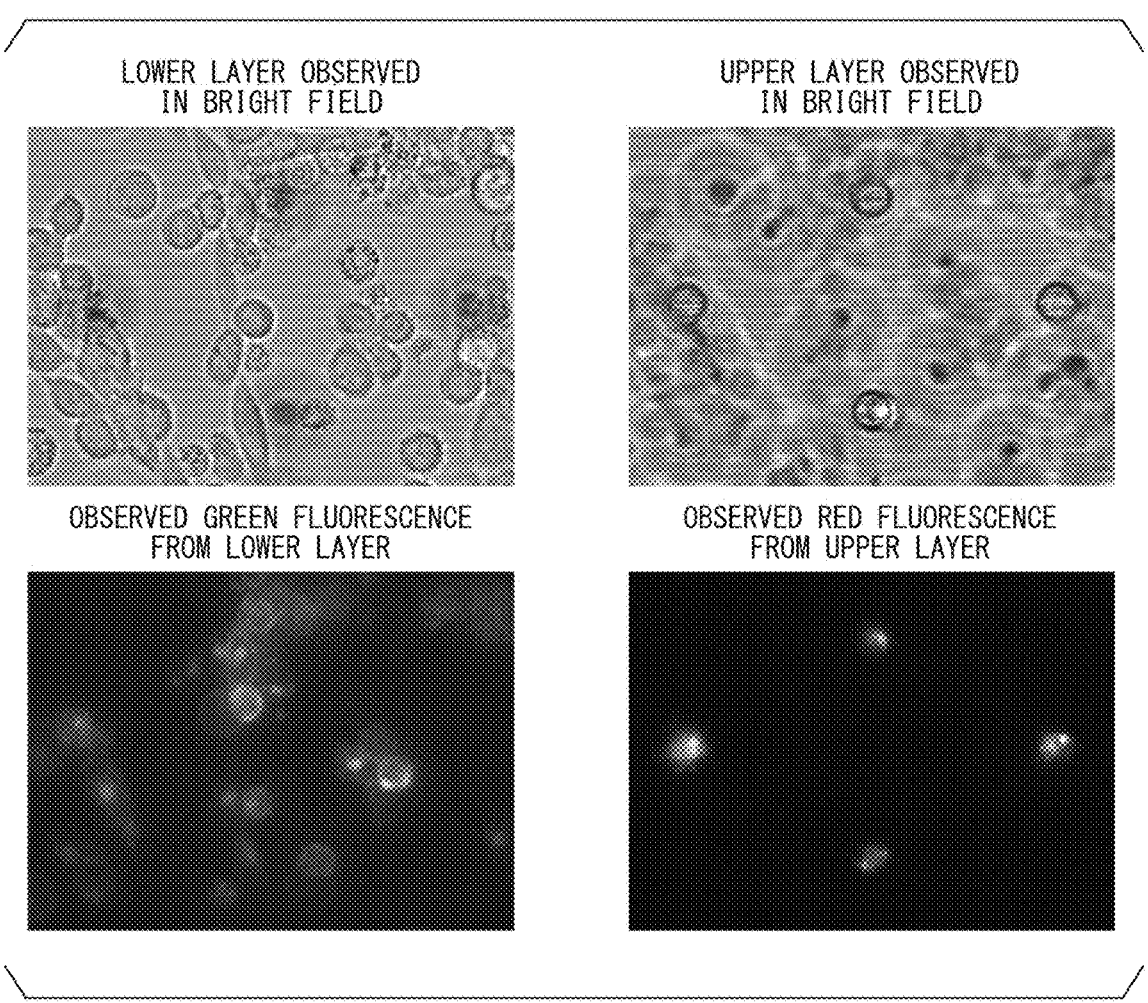
FIG. 14 is a view showing results of examples.

FIG. 14 shows fluorescence images of the structure observed from the second substrate side. By detecting a green fluorescent signal from the CHO-DG44 cells stably expressing a membrane protein that were on the second substrate, the Ba/F3 cells stably expressing mouse anti-membrane protein antibodies on the first substrate that were stained with a red fluorescent dye were identified.

Through the steps described above, a cell-sorting method could be embodied which is for sorting a target cell secreting secretions from a plurality of cells and includes a step A of dispersing the cells in a first substrate and causing the cells to be captured in depressions, the first substrate including a plurality of depressions each of which has a size that enables each of the depressions to capture one unit of a cell and in which at least some of the depressions have communication holes which communicate with one side and the other side of the first substrate and each of which has a size that enables the secretions secreted from the cells to move through each of the communication holes, a step B of causing the cells to secrete the secretions, moving the secretions through the communication holes, and accumulating the secretions moving through the communication holes in accumulation portions of the second substrate, a step C of performing detection of a change that occurs in the accumulation portions, and a step D of identifying the target cell by using a result of the detection as an indicator.

1, 2 . . . structure, 4a, 4b . . . flow channel, 10a . . . layer, 10b . . . layer, 10 . . . first substrate, 11 . . . depression, 12 . . . communication hole, 13 . . . accumulation portion, 20 . . . second substrate, 21 . . . support (substrate body), 22, . . . pillar, B . . . cell, C . . . secretions, D . . . membrane protein-expressing cell

The invention claimed is:

1. A structure comprising:
a first substrate; and
a second substrate disposed to face one side of the first substrate,
wherein the first substrate has a plurality of depressions which are open to the other side of the first substrate and each of which has a size that enables each of the depressions to capture one unit of a cell,
at least some of the depressions have only 2 to 4 communication holes per one depression, the communication holes communicating with one side and the other side of the first substrate and each of which has a size that enables secretions secreted from the cell to move through each of the communication holes,
the second substrate includes a supporting member which supports the first substrate, and accumulation portions in which the secretions moving through the communication holes are accumulated,
the one side of the second substrate that faces first substrate has a generally flat major surface,
the accumulation portions are formed in a space defined by the second substrate and the supporting member, and the accumulation portions include a fixed layer containing a substance having an affinity with the secretions secreted from one unit of the cell, and corresponds to the depressions,
the first substrate and the second substrate are made of a transparent material, and
the first substrate is made of a polymer of a curable resin composition.

2. The structure according to claim 1 that is used for dispersing the cell, causing the cell to be captured in the depressions, accumulating the secretions secreted from the cell in the accumulation portions through the communication holes, and performing detection of a change that occurs in the accumulation portions.

3. The structure according to claim 1, wherein each of the depressions has a diameter of 1 to 100 μm and includes the communication holes that are controlled,
in a case where the communication holes have a circular shape, a diameter thereof is 10 to 2,000 nm,
in a case where the communication holes have a palisade shape, a width thereof is 10 to 2,000 nm,
in a case where the communication holes have a lattice shape, a length of one side thereof is 10 to 2,000 nm, and
a thickness of the first substrate is 5 to 100 μm.

4. The structure according to claim 1, further comprising:
flow channels for removing a substance nonspecifically binding to the accumulation portions.

5. The structure according to claim 1, wherein the positions of the first substrate and the second substrate are fixed.

6. The structure according to claim 1, wherein the cell is an antibody-producing cell.

7. The structure according to claim 1, wherein the accumulation portions include a biomolecule-expressing cell having affinity with the secretions, a biomolecule having affinity with the secretions, or a compound having affinity with the secretions.

8. The structure according to claim 1, wherein a solution moves to the second substrate from the first substrate and/or to the first substrate from the second substrate through the communication holes.

9. The structure according to claim 1, wherein at least a portion of the structure includes a polymer of a curable resin composition containing (a) polyfunctional epoxy resin and (b) cationic polymerization initiator.

10. The structure according to claim 9, wherein the curable resin composition does not have cytotoxicity and autofluorescence.

11. The structure according to claim 9, wherein the curable resin composition has undergone a hydrophilizing treatment.

12. A method for manufacturing the structure according to claim 1, comprising:
- a step 1 of forming a first curable resin film by coating a first support with a first curable resin composition so as to obtain a second substrate;
- a step 2 of forming a soluble underlayer film on a second support, coating the underlayer film with a second curable resin composition so as to form a second curable resin film, and patterning communication holes on the second curable resin film so as to obtain a supporting layer having patterned communication holes;
- a step 3 of coating the supporting layer with a third curable resin composition so as to form a third curable resin film and patterning depressions on the third curable resin film so as to obtain a first substrate having patterned depressions;
- a step 4 of peeling the first substrate from the second support by dissolving the underlayer film; and
- a step 5 of bonding the first substrate and the second substrate to each other.

13. The structure-manufacturing method according to claim 12, wherein in the step 1, the supporting layer having patterned communication holes is obtained by performing exposure of the first curable resin film and then developing the first curable resin film.

14. The structure-manufacturing method according to claim 12, wherein in the step 2, the first substrate having the patterned depressions including the communication holes is obtained by performing exposure of the second curable resin film and then developing the second curable resin film.

15. The structure-manufacturing method according to claim 12, wherein in the step 4, the second substrate having patterned pillars is obtained by performing exposure of the first curable resin film and then developing the first curable resin film.

* * * * *